United States Patent
Pottier et al.

(10) Patent No.: US 11,471,482 B2
(45) Date of Patent: *Oct. 18, 2022

(54) NANOPARTICLES FOR USE IN ENHANCING BRAIN PERFORMANCES OR IN TREATING STRESS

(71) Applicant: NANOBIOTIX S.A., Paris (FR)

(72) Inventors: Agnès Pottier, Paris (FR); Laurent Levy, Paris (FR); Marie-Edith Meyre, Saint Mande (FR)

(73) Assignee: NANOBIOTIX S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/955,096

(22) PCT Filed: Dec. 18, 2018

(86) PCT No.: PCT/EP2018/085689
§ 371 (c)(1),
(2) Date: Jun. 18, 2020

(87) PCT Pub. No.: WO2019/121813
PCT Pub. Date: Jun. 27, 2019

(65) Prior Publication Data
US 2020/0405750 A1 Dec. 31, 2020

(30) Foreign Application Priority Data

Dec. 19, 2017 (EP) .................................. 17306831

(51) Int. Cl.
| | | |
|---|---|---|
| A61K 9/51 | (2006.01) |
| A61K 33/242 | (2019.01) |
| A61K 9/00 | (2006.01) |
| A61K 33/243 | (2019.01) |
| B82Y 5/00 | (2011.01) |

(52) U.S. Cl.
CPC .......... *A61K 33/242* (2019.01); *A61K 9/0085* (2013.01); *A61K 9/5115* (2013.01); *A61K 33/243* (2019.01); *B82Y 5/00* (2013.01)

(58) Field of Classification Search
CPC ................................ A61K 9/5115; B82Y 5/00
See application file for complete search history.

(56) References Cited

U.S. PATENT DOCUMENTS

| | | | |
|---|---|---|---|
| 9,034,392 | B2 | 5/2015 | Reed et al. |
| 2010/0113358 | A1 | 5/2010 | Tezapsidis et al. |
| 2014/0056813 | A1 | 2/2014 | Pottier et al. |
| 2016/0051481 | A1 | 2/2016 | Ferrari et al. |
| 2017/0290916 | A1 | 10/2017 | Kaushik et al. |
| 2017/0348350 | A1 | 12/2017 | Mortenson et al. |
| 2019/0351057 | A1 | 11/2019 | Pottier et al. |
| 2019/0351231 | A1 | 11/2019 | Meyre et al. |
| 2020/0086120 | A1 | 3/2020 | Levy et al. |
| 2021/0015756 | A1 | 1/2021 | Meyre et al. |

FOREIGN PATENT DOCUMENTS

| | | |
|---|---|---|
| RU | 2 552 957 | 6/2015 |
| WO | WO 2018/114945 | 6/2018 |
| WO | WO 2019/121748 | 6/2019 |

OTHER PUBLICATIONS

Ali, T. et al. "Anthocyanin-Loaded PEG-Gold Nanoparticles Enhanced the Neuroprotection of Anthocyanins in an Aβ$_{1-42}$ Mouse Model of Alzheimer's Disease" *Mol Neurobiol.*, 2017, pp. 6490-6506, vol. 54, No. 8.

Bharadwaj, V. N. et al. "Nanoparticle-Based Therapeutics for Brain Injury" *Advanced Healthcare Materials*, 2018, pp. 1-16, vol. 7, No. 1.

Brambilla, D. et al. "Colloidal properties of biodegradable nanoparticles influence interaction with amyloid-β peptide" *Journal of Biotechnology*, 2011, pp. 338-340, vol. 156, No. 4.

Dante, S. et al. "Selective Targeting of Neurons with Inorganic Nanoparticles: Revealing the Crucial Role of Nanoparticle Surface Charge" *ACS Nano*, 2017, pp. 6630-6640, vol. 11, No. 7.

Dkhil, M. A. et al. "Impact of gold nanoparticles on brain of mice infected with *Schistosoma mansoni*" *Parasitol Res.*, 2015, pp. 3711-3719, vol. 114, No. 10.

Moore, K. A. et al. "Influence of gold nanoparticle surface chemistry and diameter upon Alzheimer's disease amyloid-β protein aggregation" *Journal of Biological Engineering*, 2017, pp. 1-11, vol. 11, No. 5.

Muller, A. P. et al. "Gold nanoparticles prevent cognitive deficits, oxidative stress and inflammation in a rat model of sporadic dementia of Alzheimer's type" *Materials Science and Engineering C*, 2017, pp. 476-483, vol. 77.

Naziroglu, M. et al. "Nanoparticles as potential clinical therapeutic agents in Alzheimer's disease: Focus on selenium nanoparticles" *Expert Review of Clinical Pharmacology*, 2017, pp. 1-32.

(Continued)

*Primary Examiner* — Robert S Cabral
(74) *Attorney, Agent, or Firm* — Saliwanchik, Lloyd & Eisenschenk

(57) ABSTRACT

The present invention relates to the medical field, in particular to the enhancement of brain performances and for the treatment of pathological stress. More specifically the present invention relates to a nanoparticle or nanoparticles' aggregate for use in enhancing brain performances or in prevention or treatment of pathological stress in a subject without exposure of the nanoparticle or nanoparticles' aggregate to an electric field, and preferably without exposure thereof to any other external activation source, wherein the nanoparticle's or nanoparticles' aggregate's material is selected from a conductor material, a semiconductor material, an insulator material with a dielectric constant $\varepsilon_{ijk}$ equal to or above (200), and an insulator material with a dielectric constant $\varepsilon_{ijk}$ equal to or below (100). It further relates to compositions and kits comprising such nanoparticles and/or nanoparticles' aggregates as well as to uses thereof without exposure thereof to an electric field, and preferably without exposure thereof to any other external activation source such as a light source, a magnetic field, or an ultrasound source.

10 Claims, 5 Drawing Sheets

(56) References Cited

OTHER PUBLICATIONS

Figure 1:
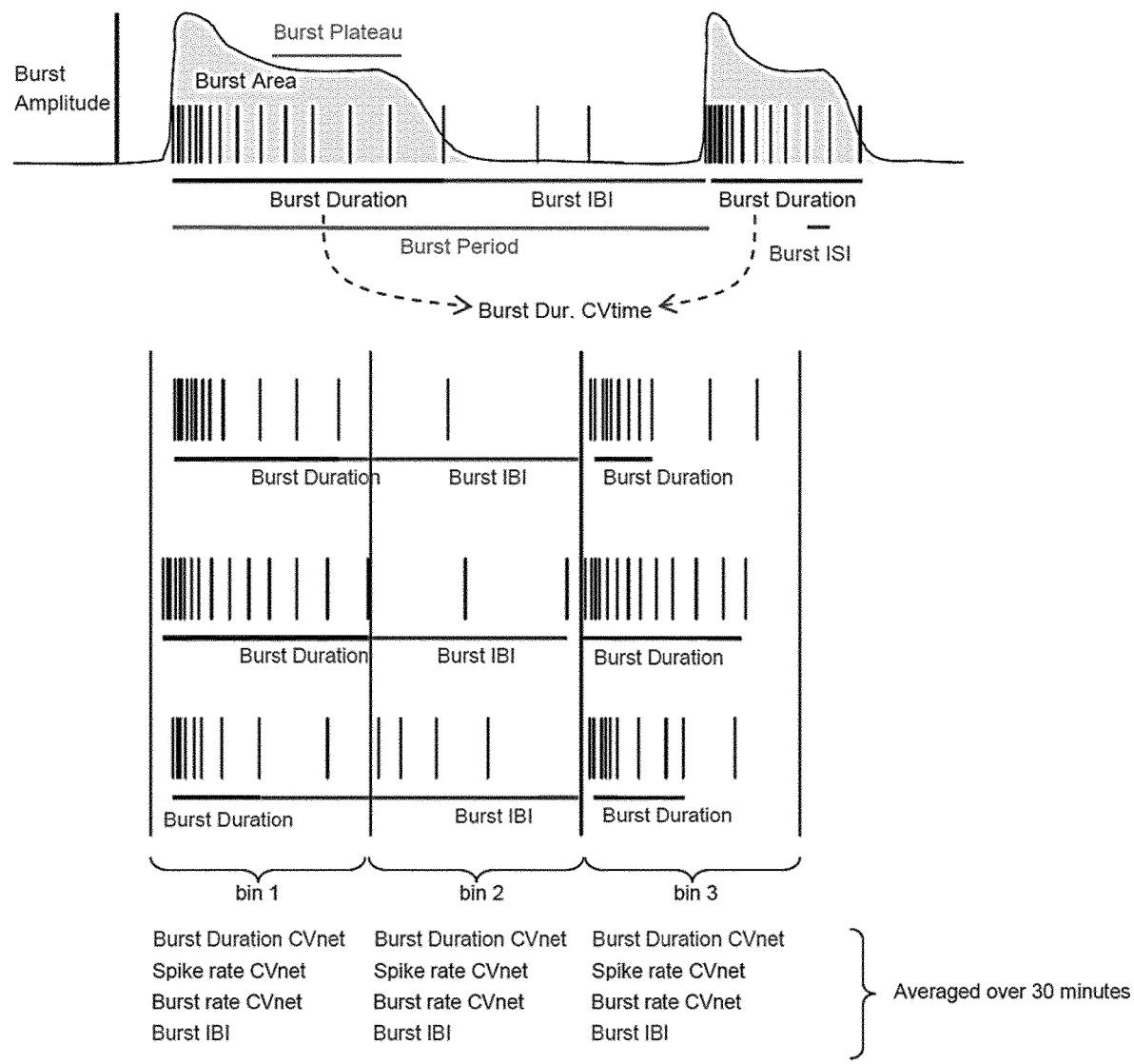

Thakur, G. et al. "Conjugated Quantum Dots Inhibit the Amyloid β (1-42) Fibrillation Process" *International Journal of Alzheimer's Disease*, Mar. 2, 2011, pp. 1-15, vol. 2011, Article ID 502386.
Written Opinion in International Application No. PCT/EP2018/085689, dated Mar. 21, 2019, pp. 1-12.
Allowed claims in U.S. Appl. No. 16/472,214, 2021, pp. 1-3.
Allowed claims in U.S. Appl. No. 16/472,215, 2021, pp. 1-4.
Allowed claims in U.S. Appl. No. 16/472,216, 2021, pp. 1-3.
Ahmad, A. F. et al. "Chemically Reduced Graphene Oxide-Reinforced Poly(Lactic Acid)/Poly(Ethylene Glycol) Nanocomposites: Preparation, Characterization, and Applications in Electromagnetic Interference Shielding" *Polymers*, Apr. 11, 2019, pp. 1-20, vol. 11, No. 661.
Elizalde, N. et al. "Long-lasting behavioral effects and recognition memory deficit induced by chronic mild stress in mice: effect of antidepressant treatment" *Psychopharmacology*, 2008, pp. 1-14, vol. 199.
Berlin, J. M. et al. "Effective Drug Delivery, in vitro and in vivo, By Carbon-Based Nanovectors Non-Covalently Loaded With Unmodified Paclitaxel" *ACS Nano*, Aug. 24, 2010, pp. 1-36, vol. 4, No. 8.
Bitner, B. R. et al. "Antioxidant Carbon Particles Improve Cerebrovascular Dysfunction Following Traumatic Brain Injury" *ACS Nano*, Sep. 25, 2012, pp. 1-17, vol. 6, No. 9.
Wang, S. et al. "The role of $sp^2/sp^3$ hybrid carbon regulation in the nonlinear optical properties of graphene oxide materials" *RSC Advances*, 2017, pp. 53643-53652, vol. 7.
Kim, K.-M. et al. "Surface treatment of silica nanoparticles for stable and charge-controlled colloidal silica" *International Journal of Nanomedicine*, 2014, pp. 29-40, vol. 9, Suppl. 2.
Zamiri, R. et al. "Dielectrical Properties of $CeO_2$ Nanoparticles at Different Temperatures" *PLoS ONE*, Apr. 24, 2015, pp. 1-11, vol. 10, No. 4, e0122989.
Johnson, D. "Silicon Nanoparticles Provide Biocompatible Solution to Cancer Detection and Treatment, Porous silicon nanoparticles offer harmless diagnostic and therapeutic solution for many types of cancer" IEEE Spectrum, Jul. 22, 2016, pp. 1-5, abstract only.

NANOPARTICLES FOR USE IN ENHANCING BRAIN PERFORMANCES OR IN TREATING STRESS

CROSS-REFERENCE TO RELATED APPLICATION

This application is the U.S. national stage application of International Patent Application No. PCT/EP2018/085689, filed Dec. 18, 2018.

The present invention relates to the medical field, in particular to the enhancement of brain performances and to the treatment of pathological stress. More specifically the present invention relates to a nanoparticle or nanoparticles' aggregate for use in enhancing brain performances or in prevention or treatment of pathological stress in a subject without exposure of the nanoparticle or nanoparticles' aggregate to an electric field, and preferably without exposure thereof to any other external activation source such as a light source, a magnetic field, or an ultrasound source, wherein the nanoparticle's or nanoparticles' aggregate's material is selected from a conductor material, a semiconductor material, an insulator material with a dielectric constant $\varepsilon_{ijk}$ equal to or above 200, and an insulator material with a dielectric constant $\varepsilon_{ijk}$ equal to or below 100. It further relates to compositions and kits comprising such nanoparticles and/or nanoparticles' aggregates as well as to uses thereof without exposure thereof to an electric field, and preferably without exposure thereof to any other external activation source such as a light source, a magnetic field, or an ultrasound source.

BACKGROUND

With advancing comprehension of neuroscience, brain can be thought as an electric network, coding and transmitting information through its electric wires, neurons. Connectivity between neurons is simple and complex at the same time: simple because it lies on influx/efflux of ions inside neurons, which result in action potentials (or "spikes" of electric activity); complex because the brain network is composed of hundreds of billion neurons, which form nodes, hubs and modules that demonstrate coordinated interactions, at various spatial and temporal scales (Fornito et al., *Nature Reviews Neuroscience*, 2015, 16, 159-172: *The connectomics of brain disorders*). Neural communication depends on the anatomical components that connect individual neurons (structure) and on the process of transmitting information (function). Both aspects affect the overall performance of the nervous system. Neuronal interactions are traduced by oscillations of the brain electric activity pattern, which oscillations are measurable typically by electroencephalogram (EEG). Different frequency bands of oscillations are observed: delta, theta, alpha, beta, gamma (Ward et al., *Trends in Cognitive Sciences*, 2003, 7(12), 553-559: *Synchronous neural oscillations and cognitive processes*). Structurally, the most striking neuroanatomical feature of the brain is the abundant connectivity between neurons, which reflects the importance of neural communication. Synchronization of oscillations ("synchrony") between one brain area and another seems to constitute the last level of information coding [first level (neuron): action potentials; second level (neuronal network(s)): neuronal oscillations] by bringing spatio-temporal coordination (Engel et al., *Nature Reviews Neuroscience*, 2001, 2, 704-716: *Dynamic predictions: oscillations and synchrony in top-down processing*). Importantly, evidence is emerging that a delicately balanced pattern of synchronization and desynchronization in space and time is fundamental to the functional performance of the nervous system (Schnitzler et al., *Nature Reviews Neuroscience*, 2005, 6, 285-296: *Normal and pathological oscillatory communication in the brain*).

The development of specific skills, creativity or idea generation in certain individuals and not others is something very puzzling and which is still not explained. However, the study of certain diseases and of their symptoms may help understanding the functioning of "normal" and "abnormal" brains. For example, it has been observed that individuals with a neurodegenerative disease like frontotemporal dementia develop drawing and painting skills with the advancement of their disease (Miller et al., *Neurology*, 1998, 978-982: *Emergence of artistic talent in frontotemporal dementia*). Several publications demonstrate that the propensity to suffer from a neurological disease, like bipolar syndrome, schizophrenia or autism, is higher for people (and their first-degree relatives) working in a creative domain (engineering, literature, painting), than for "non-creative people" (Andreasen N. C., *American Journal of Psychiatry*, 1987, 144(10), 1288-1292: *Creativity and mental illness: prevalence rates in writers and their first-degree relatives*; Baron-Cohen et al., *Autism*, 1997, 101-109: *Is there a link between engineering and autism*; Sussman et al., *Stanford Journal of Neuroscience*, 2007, 1(1), 21-24: *Mental illness and creativity: a neurological view of the "tortured artist"*). Several models have been elaborated to describe the process of creation and idea generation: the hemispheric model, which suggests that the non-dominant hemisphere is specialized for creative activity, or more recently the frontotemporal model, which suggests that changes in the temporal lobe may increase idea generation whereas changes in the frontal lobe may decrease it (Flaherty et al., *J Comp Neurol*, 2005, 493(1), 147-153: *Frontotemporal and dopaminergic control of idea generation and creative drive*). Indeed, certain savants can perform esoteric numerical calculations while being deficient in elementary arithmetic (Snyder et al., *Proceedings of the Royal Society of London B*, 1999, 266, 587-592: *Is integer arithmetic fundamental to mental processing?: the mind's secret arithmetic*). Interestingly, there is evidence that such unusual ability is related with left (dominant) hemisphere inhibition together with right (non-dominant) hemisphere facilitation (Treffert D. A., *Philosophical Transactions of the Royal Society B*, 2009, 364, 1351-1357: *The savant syndrome: an extraordinary condition. A synopsis: past, present, future*).

Thus, brain is a dynamic system, where specific states of cerebral functioning derive from complex excitatory and inhibitory interactions between neuronal populations. Then, an "abnormal" state reflects an imbalance between complex excitatory and inhibitory interactions between neuronal populations (Kapur et al., *Brain*, 1996, 119, 1775-1790: *Paradoxical functional facilitation in brain-behaviour research, a critical review*).

The present invention deals with nanoparticles and/or nanoparticles' aggregates (aggregates of nanoparticles) for use in enhancing, increasing or improving brain performances/capacities or for preventing or treating/for use in prevention or treatment of pathological stress or at least one symptom thereof.

The nanoparticles and aggregates of nanoparticles herein described by inventors do not require the application/induction of an electric current or field/stimulus, and preferably do not require exposure to any other external activation source such as a light source, a magnetic field, or an ultrasound source, to exert their function (i.e. to be efficient). The herein described nanoparticles and aggregates of nanoparticles do not require to be exposed to an electric current or field/stimulus, and preferably do not require to be exposed to any other external activation source such as a light source, a magnetic field, or an ultrasound source, to be functional in the context of the herein described uses. Inventors have discovered that these nanoparticles or aggregates of nanoparticles can advantageously and surprisingly be used efficiently without being exposed, or without exposure of the subject they are administered to, to an electric current or field/stimulus, typically to an electric current or field/stimulus applied to said subject for example by transcranial electric stimulation (TES) or by transcranial magnetic stimulation (TMS), and preferably without exposure to any other external activation source such as a light source, a magnetic field, or an ultrasound source. This means that the treated subject will not suffer the negative side effects of exposure to an electric current or field/stimulus or to any other external activation source such as a light source, a magnetic field, or an ultrasound source, thanks to the present invention.

As well known by the skilled person in the art, a nanoparticle has an elevated/high surface/volume ratio, typically approximately 35%-40% of atoms are localized at the surface of a 10 nm-nanoparticle compared with less than 20% for a nanoparticle having a size above 30 nm. This high surface/volume ratio is associated with a strong surface reactivity that is size-dependent. As a result, nanoparticles (especially those smaller than 20 nm) may exhibit novel properties compared with bulk materials. For instance, gold particles are known to be chemically inert and resistant to oxidation at a macroscopic scale, while gold particles having a size below 10 nm have a chemically active surface. The toxic mechanisms associated with the chemical destabilization of metallic nanoparticles might be (i) the direct release of metals in solutions (dissolution process), (ii) the catalytic properties of metallic nanoparticles, and (iii) the redox evolution of the nanoparticle's surface, which can oxidize proteins, generate reactive oxygen species (ROS) and induce an oxidative stress (cf. M. Auffan et al., *Environmental Pollution* 157 (2009) 1127-1133: *Chemical Stability of metallic nanoparticles: a parameter controlling their potential cellular toxicity in vitro*).

Beside herein above described gold nanoparticles which present catalytic properties, cerium oxide (7 nm-$CeO_2$ particle) or iron oxide (20 nm-$Fe_3O_4$ particle) nanoparticles have shown redox modification of their surface leading to cytotoxic effects related to an oxidative stress in vitro (cf. M Auffan et al., *Environmental Pollution* 157 (2009) 1127-1133: *Chemical Stability of metallic nanoparticles: a parameter controlling their potential cellular toxicity in vitro*). As well, 11 nm-silica nanostructure is eroded by biological media (cf. S-A Yang et al., *Scientific Reports* 2018 8:185: Silica nanoparticle stability in biological media revisited).

As herein below explained by inventors, nanoparticle having a size below 30 nm, are thus to be carefully selected when intended to be used in vivo in a subject, typically in a mammal, in particular in a human being.

BRIEF DESCRIPTION

Herein advantageously described for the first time is a nanoparticle or nanoparticles' aggregate for use in enhancing, increasing, or improving brain performances/capacities or for preventing or treating/for use in prevention or treatment of pathological stress or at least one symptom thereof in a subject without exposure of the nanoparticle or nanoparticles' aggregate to an electric field, and preferably without exposure thereof to any other external activation source such as a light source, a magnetic field, or an ultrasound source. The nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

Inventors herein describe, in a particular aspect, a nanoparticle or nanoparticles' aggregate for use in enhancing brain performances or for use in prevention or treatment of pathological stress in a subject without exposure of the nanoparticle or nanoparticles' aggregate to an electric field nor to any other external activation source, wherein the nanoparticle's or nanoparticles' aggregate's material is selected from a conductor material, a semiconductor material, an insulator material with a dielectric constant $\varepsilon_{ijk}$ equal to or above 200, and an insulator material with a dielectric constant $\varepsilon_{ijk}$ equal to or below 100, wherein i) the median largest size of the core of the nanoparticle or nanoparticles' aggregate of the population is of at least 30 nm when the material is a conductor material, a semiconductor material or an insulator material with a dielectric constant $\varepsilon_{ijk}$ equal to or above 200, and wherein ii) the core of the nanoparticle or nanoparticles' aggregate is coated with a biocompatible coating providing a neutral or a negative surface charge when measured in a solution of water having a concentration of electrolytes between 0.001 and 0.2 M, a concentration of the nanoparticles' or nanoparticles' aggregates' material between 0.01 and 10 g/L and a pH between 6 and 8.

Also herein described is the use of a nanoparticle or nanoparticles' aggregate for preparing a composition for enhancing, increasing, or improving brain performances/capacities or for preventing or treating pathological stress or at least one symptom thereof in a subject in need thereof without exposure of the nanoparticle or nanoparticles' aggregate to an electric field, and preferably without exposure thereof to any other external activation source such as a light source, a magnetic field, or an ultrasound source.

Also herein described is a composition for use in enhancing brain performances or for preventing or treating/for use in prevention or treatment of pathological stress or at least one symptom thereof in a subject, wherein the composition comprises, or consists of, nanoparticles and/or nanoparticles' aggregates and a pharmaceutically acceptable support, wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100, and wherein the enhancement of brain performance or the prevention or treatment of pathological stress is performed without exposure to an electric field of the nanoparticles or nanoparticles' aggregates administered to the subject through the composition, and preferably without exposure thereof to any other external activation source such as a light source, a magnetic field, or an ultrasound source.

Further herein described is a kit comprising, or consisting of, at least two distinct nanoparticles and/or nanoparticles' aggregates, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100, and uses thereof typically in enhancing brain performances or in a method for enhancing brain performances, or in prevention or treatment of pathological stress or at least one symptom thereof in a subject without exposure of the nanoparticles or nanoparticles' aggregates to an electric field, and preferably without exposure thereof to any other external activation source such as a light source, a magnetic field, or an ultrasound source.

DETAILED DESCRIPTION

The human nervous system is estimated to consist of roughly 80-120 billion nerve cells (Herculano-Houzel S. *Frontier in Human Neuroscience* (2009), 3(31): 1-11: *The human brain in numbers: a linearly scaled-up primate brain*). The defining characteristic of a neuron (or nerve cell) is its ability to transmit electrical signals in the form of action potentials.

The neuron/nerve cell constitutes the elementary node of the brain. The structure of a neuron/nerve cell consists of: the "soma" or "cell body", which contains the nucleus and can be prolonged by dendrites, the "axon", which transmits the electrical signal, and the axon terminal, which consists of the synaptic terminals.

Nerve cells can communicate with each other in a highly-structured manner forming neuronal networks.

Neuron communicates via synaptic connections. Within neuron, nanocircuits constitute the underlying biochemical machinery for mediating key neuronal properties such as learning and memory and the genesis of neuronal rhythmicity.

A microcircuit can be formed with just only a few interconnected neurons and can perform sophisticated tasks such as mediate reflexes, process sensory information, initiation of locomotion, and learning and memory mediation. A macrocircuit is a more complex network which consists of multiple imbedded microcircuits. Macrocircuits mediate higher brain functions such as object recognition and cognition.

So, multiple levels of networks occupy the nervous system.

Neural Network Excitability

Neurons send messages electrochemically (i.e. chemicals/ions cause an electrical signal). The important ions in the nervous system are sodium and potassium, calcium and chloride. When a neuron is not sending a signal, it is "at rest." When a neuron is at rest, the inside of the neuron is negative relative to the outside. Although the concentrations of the different ions attempt to balance out on both sides of the membrane, they cannot because the cell membrane allows only some ions to pass through channels (ion channels). In addition to these selective ion channels, there is a pump that uses energy to move three sodium ions out of the neuron for every two potassium ions it puts in. Finally, when all these forces balance out, and the difference in the voltage between the inside and outside of the neuron is measured, the resting membrane potential (also "resting potential") of a neuron is about −70 mV. This means that the inside of the neuron is 70 mV less than the outside. At rest, there are relatively more sodium ions outside the neuron and more potassium ions inside that neuron. An action potential (also identified as "spike" or "impulse") occurs when a neuron sends information down an axon, away from the cell body. This means that some event (a stimulus) causes the resting potential to move toward 0 mV. When the depolarization reaches about −55 mV the neuron fires an action potential. If the depolarization does not reach this critical threshold level, then no action potential fires (on/off mechanism). Also, when the threshold level is reached, an action potential of fixed amplitude always fires. Therefore, either the depolarization does not reach the threshold or a full action potential is generated.

A great variability is found in the velocity of the propagation of action potentials. In fact, the propagation velocity of the action potentials in nerves can vary from 100 meters per second to less than a tenth of a meter per second. Whereas the time constant is an index of how rapidly a membrane will respond to a stimulus in time, the space constant (also length constant) is an index of how well an electric potential will spread along an axon as a function of distance.

Structure of the Cerebral Cortex

There are two broad classes of cortical neurons: "inhibitory neurons" or "interneurons", which make only short-range, local connections; and "excitatory neurons" or "projection neurons" or "pyramidal neurons", which extend axons to distant intracortical, subcortical and subcerebral targets. "Inhibitory neurons" or "interneurons" constitute a minority (20%) of the cortical neurons; the majority is contained in "pyramidal neurons" (Shipp S., *Current Biology*, 2007, 17(12), R443-449: *Structure and function of the cerebral cortex*). Projection neurons are glutamatergic neurons that transmit information between different regions of the neocortex and to other regions of the brain (Bikson et al., *J Physiol*, 2004, 557(1), 175-190: *Effects of uniform extracellular DC electric fields on excitability in rat hippocampal slices in vitro*). Projection neurons or pyramidal neurons are named for their prominent apical dendrite, which typically points superficially, providing them a pyramidal morphology. Customarily, a neuron "belongs" to the layer in which its cell body (or "soma") is sited—even if the apical and basal dendrites, between them, span several more layers, picking up a broader range of signals (Shipp S., *Current Biology*, 2007, 17(12), R443-449: *Structure and function of the cerebral cortex*).

The grey matter of the cerebral cortex is a convoluted, layered sheet of tissue, 2-3 millimeters thick in man but with a surface area of several hundred square centimeters (Shipp S., *Current Biology*, 2007, 17(12), R443-449: *Structure and function of the cerebral cortex*). Six major layers are recognized in the cerebral cortex:

Layer I, the molecular layer, contains few scattered neurons and consists mainly of extensions of apical dendritic tufts of pyramidal neurons and horizontally oriented axons, as well as glial cells;

Layer II, the external granular layer, contains predominantly small and medium-size pyramidal neurons and numerous stellate neurons;

Layer III, the external pyramidal layer, contains predominantly small and medium-size pyramidal neurons, as well as non-pyramidal neurons with vertically oriented intracortical axons;

Layer IV, the internal granular layer, contains different types of stellate and pyramidal neurons;

Layer V, the internal pyramidal layer, contains large pyramidal neurons which give rise to axons leaving the cortex and running down to subcortical structures (such as the basal ganglia). In the primary motor cortex of the frontal lobe, layer V contains cells whose axons travel through the internal capsule, the brain stem and the spinal cord forming the corticospinal tract, which is the main pathway for voluntary motor control; and Layer VI, the polymorphic or multiform layer, contains few large pyramidal neurons and many small spindle-like pyramidal and multiform neurons; layer VI send efferent fibers to the thalamus, establishing a very precise reciprocal interconnection between the cortex and the thalamus.

These layers are differently developed in various regions of the cerebral cortex, e.g. pyramidal layers are more developed in the motor centers and granular layers in sensory centers of the cerebral cortex.

Connectivity Within and Between Neuronal Networks

There are three connectivity network types that are used to investigate communication within and across the brain. Structural connectivity is based on the detection of the fiber tracks that physically connect the regions of the brain. These are the anatomical network maps that indicate possible pathways that the signals can travel on in the brain. Functional connectivity identifies activity in brain regions that have similar frequency, phase and/or amplitude of correlated activity. Effective connectivity uses the functional connectivity information and goes one step further in determining the direct or indirect influence that one neural system may have over another, more specifically the direction of the dynamic information flow in the brain (Bowyer et al., *Neuropsychiatric Electrophysiology*, 2016, 2(1), 1-12: *Coherence a measure of the brain networks: past and present*.).

The synchronized activity within a neuronal network can be detected by magnetoencephalogram (MEG), electroencephalogram (EEG), Functional Magnetic Resonance Imaging (FMRI) or Positron Emission Tomography (PET), then image using network connectivity analysis. MEG (Magnetoencephalogram) or EEG (Electroencephalogram) are preferred because they have high temporal resolution to resolve the dynamic flow of information. Connectivity analysis of the brain is performed to map out the communication networks needed for the brain to function. Specific regions in the brain are specialized for processing certain types of information. Imaging techniques have revealed that these regions are connected and communicate with other specialized regions across networks in the brain. "Coherence" (Bowyer et al.) is a mathematical technique that quantifies the frequency and amplitude of the synchronicity (the state of being in synchrony or of being synchronized) of neuronal patterns of oscillating brain activity. Detection of the synchronous activation of neurons can be used to determine the wellbeing or integrity of the functional connectivity in the human brain. Overlaying the functional connectivity maps onto the structural connectivity images and the using direction of information flow derived from effective connectivity provides an all-inclusive understanding of how the brain functions.

The intact brain (i.e. "normal" or "healthy") expresses complex patterns of (i.e. "normal" or "healthy") synchronous activity, associated with different 'states' of the organism, from slow delta rhythm (0.5-4 Hz), through theta (4-8 Hz), alpha (8-12 Hz), beta (15-30 Hz) and gamma (30-70 Hz) oscillations. Interestingly, the dissociated culture of cortical structures offers a convenient system for the examination of the rules that govern the emergence, generation and spread of network firing (spikes) and bursting (clusters of spikes) in populations of densely interconnected neurons. Network activity can be recorded for extended periods of time in a non-invasive manner and with finite time resolution using multielectrodes arrays. The 2-dimensional dissociated culture can be used as a viable test system for studying rules that govern the formation and maintenance of network activity in the brain, allowing the testing of hypothesis that cannot be addressed in the intact brain (Cohen E. et al., *Brain Research*, 2008, 1235, 21-30: *Determinants of spontaneous activity in networks of cultured hippocampus*).

Human mental abilities or brain performances, such as intelligence, are particularly complex.

Understanding these abilities in mechanistic terms has the potential to facilitate their enhancement.

Studies using encephalograms and event-related potentials indicate that the speed and reliability of neural transmission are related to higher performances, typically to higher intelligence. Early neuroimaging studies using PET found that intelligence correlated negatively with cerebral glucose metabolism during mental activity, leading to the formulation of a 'neural efficiency' hypothesis.

According to this hypothesis, more intelligent individuals expend fewer neuronal resources to perform at a given level. Intelligence in the sense of reasoning and novel problem-solving ability is consistently linked to the integrity, structure and function of the lateral prefrontal cortex, and possibly to that of other areas. Outstanding questions about the neural bases of intelligence include among others the relationships between psychometric intelligence (i.e. intelligence as measured by an IQ-type test, typically assessing the accuracy of a response (and not the speed)) and (i) functional connectivity between components of working memory networks as indicated by electroencephalogram-based studies and (ii) neural plasticity (i.e. used to refer to those processes that involve major connectional changes of the nervous system in response to experience and that are observed to cease to operate at maturity in human). The development of neural connections was reported to be consistent with the development of intelligence (Gray J. R. et al., *Nature Review Neuroscience*, 2004, 5, 471-482: *Neurobiology of intelligence: science and ethics*; Garlick D., *Psychological Review*, 2002, 109(1), 116-136: *Understanding the nature of general factor of intelligence: the role of individual difference in neural plasticity as an explanatory mechanism*.).

Communication among neurons is indeed essential for higher brain functions such as perception, memory and movement (Massobrio P et al. *Neural Plasticity*, 2015, Article ID 196195, *In vitro studies of neuronal networks and synaptic plasticity in invertebrates and in mammals using multi electrode arrays*). While the formation and development of connections is assumed to be crucial in the process of learning, their conservation appears to be essential for memory. Synaptic plasticity has long been implicated in cognitive processes such as learning and memory. Synaptic plasticity at the network level provides a distributed mechanism to convert and store temporal information into spatially distributed patterns of synaptic modifications. Each time something is learned, the network develops new connectivity and incorporates the newly learned facts.

Effective connections between neurons may be detected using typically imaging methods well known by the skilled person such as electron-based imaging methods which provide structural information about synaptic connectivity, typically electron microscopy (EM), for example serial block-face electron microscopy (SBFEM), serial section scanning electron microscopy (SSSEM), automated transmission EM (ATEM), etc.; photon-based imaging methods, for example "Brainbow" (Lichtman J W et al., *Curr Opin Neurobiol*, 2008, 22, 144-153: *Ome sweet ome: what can the genome tell us about the connectome?*; Cai D., et al., *Nat Methods*, 2013, 10(6), 540-547: *Improved tools for the Brainbow toolbox*), "array tomography" (AT) (Micheva K D., et al, 2007, *Neuron*, 55, 25-36: *Array tomography: a new tool for imaging the molecular architecture and ultrastructure of neural circuits*; Micheva K D., et al., 2010, *Neuron*, 68, 639-653: *Single-synapse analysis of a diverse synapse population: proteomic imaging methods and markers*), GFP reconstitution across synaptic partners ("GRASP"), in particular mammalian GRASP "mGRASP" (Kim J, et al., 2012, *Nat Methods*, 9(1), 96-102: *mGRASP enables mapping mammalian synaptic connectivity with light microscopy*; Feng L, et al., 2012, *Bioinformatics*, 28, i25-i31: *Improved synapse detection for mGRASP-assisted brain connectivity.*), Trans-synaptic tracing by rabies virus (Osakada F, et al., 2011, *Neuron*, 71, 617-631: *New rabies virus variants for monitoring and manipulating activity and gene expression in defined neural circuits*; Wickersham I R, et al., 2007, *Nat Methods*, 4(1), 47-49: *Retrograde neuronal tracing with a deletion-mitant rabies virus*; Wickersham I R, et al., 2007, *Neuron*, 53(5), 639-647: *Monosynaptic restriction of transsynaptic tracing from single, genetically targeted neurons*), fluorescent selective plane illumination microscopy (fSPIM) (Tomer R, et al., 2012 *Nat methods*, 9, 755-763: *Quantitative high-speed imaging of entire developing embryos with simultaneous Multiview light-sheet microscopy*; York A G, et al., 2012, *Nat Methods*, 9(7), 749-754: *Resolution doubling in live, multicellular organisms via multifocal structured illumination microscopy.*) preferably in combination with a clearing method such as "CLARITY" (Chung K, et al., 2013, *Nature*, 497 (7449), 332-337: *Structural and molecular interrogation of intact biological systems.*); as well as optogenetic methods such as channelrhodopsin and/or two-photon microscopic calcium imaging methods which allow the mapping of the spatial distribution of synaptic connections together with measures of synaptic strength (Petreanu L, et al., 2007, *Nat Neurosci*, 10, 663-668: *Channelrhodopsin-2-assisted circuit mapping of long-range callosal projections*; Wang H, et al., 2007, *Proc Natl Acad Sci USA*, 104, 8143-8148: *High-speed mapping of synaptic connectivity using photostimulation in channelrhodopsin-2 transgenic mice*) as well as the detection of active synapses innervated by different inputs (Little J P, et al., 2012, *J Neurosci: Off J Soc Neurosci*, 32(37), 12808-12819: *Subcellular synaptic connectivity of layer 2 pyramidal neurons in the medial prefrontal cortex*; MacAskill A F, et al., 2012, *Nat Neurosci*, 15(12), 1624-1626: *Subcellular connectivity underlies pathway-specific signaling in the nucleus accumbens*); or any combinations of these different methods (Yook C. et al., *Cellular and Molecular Life Sciences*, 2013, 70, 4747-4757: *Mapping mammalian synaptic connectivity*).

Herein advantageously described for the first time is a nanoparticle or nanoparticles' aggregate for use in enhancing, increasing or improving brain performances/capacities or for preventing or treating/for use in prevention or treatment of pathological stress or at least one symptom thereof without exposure of the nanoparticle or nanoparticles' aggregate to an electric field, and preferably without exposure thereof to any other external activation source such as a light source, a magnetic field, or an ultrasound source. Such an exposure to a (therapeutic or diagnostic) electric field or to any other (therapeutic or diagnostic) external activation source such as a light source, a magnetic field or an ultrasound source are typically to be herein understood as being a therapeutic or diagnostic exposure, typically performed by medical staff, for example by a physician or a nurse.

The nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

In a typical aspect, the nanoparticle or nanoparticles' aggregate herein described is for use in enhancing physical performances, or in enhancing cognitive performances, i.e. learning, memorizing, sense perception, attention and/or decision making of a subject without exposure of the nanoparticle or nanoparticles' aggregate to an electric field, and preferably without exposure thereof to any other external activation source such as a light source, a magnetic field, or an ultrasound source.

Nanoparticles

Herein described is a nanoparticle or aggregate of nanoparticles for use according to the invention in enhancing brain performances or in treating pathological stress or at least one symptom thereof in a subject without exposure of the nanoparticle or nanoparticles' aggregate to an electric field, and preferably without exposure of said nanoparticle or aggregate of nanoparticles to any other external activation source such as a light source, a magnetic field, or an ultrasound source, wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

The Nanoparticle's or Nanoparticles Aggregate'S Dimension or Size

In the spirit of the invention, the terms "nanoparticle" or "nanoparticles' aggregate" refers to a product, in particular a synthetic product, with a size in the nanometer range, typically between 1 nm and 1000 nm, or between 1 nm and 500 nm, for example between at least 10 nm and about 500 nm or about 1000 nm, between at least 30 nm and about 500 nm or about 1000 nm, between at least 40 nm and about 500 nm or about 1000 nm, between at least 45 nm and about 500 nm or about 1000 nm, preferably below 500 nm.

The term "aggregate of nanoparticles" or "nanoparticles' aggregate" refers to an assemblage of nanoparticles strongly, typically covalently, bound to each other.

Electron microscopy such as Scanning Electron Microscopy (SEM), Transmission electron microscopy (TEM), or cryo-TEM, can be used to measure the size of the nanoparticle or of the aggregate of nanoparticles, and more particularly the size of the core of the nanoparticle or nanoparticles' aggregate, i.e., the nanoparticle or nanoparticles' aggregate without its biocompatible coating. As a matter of fact, the biocompatible coating is generally made of compounds which consist mainly of light elements (polymer or organic compounds), whose elastic interactions with the energetic electrons are relatively weak, resulting in a poor image contrast. The TEM measures the projected images of particles deposited onto an electron-transparent substrate. The recording of more than about 50, preferably more than about 100, 150 or 200 nanoparticles or nanoparticles' aggregates per sample should typically be measured for size assessment. The recording of more than about 50, or preferably more than about 100, 150 or 200 nanoparticles or nanoparticles' aggregates therefore allows for establishing the median largest size of the core of the nanoparticles or nanoparticles' aggregates of the population, as well as the size of the core of the nanoparticles or nanoparticles' aggregates representing the 30%-70% percentile of the population of nanoparticles and nanoparticles' aggregates. A typical assay protocol may be found in "NIST—NCL Joint Assay Protocol, PCC-7; Measuring the size of using transmission electron microscopy (TEM); version 1.1 December 2009".

As well, dynamic light scattering (DLS) can be used to measure the hydrodynamic diameter of nanoparticles or nanoparticles' aggregates (i.e., the diameter of the nanoparticle or of the nanoparticles' aggregate including both its core and its biocompatible coating) in solution. The hydrodynamic diameter is the diameter of an equivalent hard sphere that diffuses at the same rate as the analyte. A typical assay protocol may be found in "NIST—NCL Joint Assay Protocol, PCC-1; Measuring the size of nanoparticles in aqueous media using batch-mode dynamic light scattering; version 1.1 February 2010. Particle size results obtained from DLS measurement may not coincide with those obtained from other techniques (e.g. electron microscopy). This is due in part to differences in the physical property that is actually measured (e.g. hydrodynamic diffusion versus projected area). Moreover, DLS is sensitive to the presence of small quantities of large particles or of clusters of smaller particles, whereas electron microscopy typically reflects the size of primary particles (i.e. the size of the core of the nanoparticles or nanoparticles' aggregates) (cf. NIST—NCL Joint Assay Protocol, PCC-1; Measuring the size of nanoparticles in aqueous media using batch-mode dynamic light scattering; version 1.1 February 2010).

These two methods, DLS and electron microscopy, may further be used one after each other to compare size measures and confirm said size. A preferred method for measuring nanoparticles and nanoparticles' aggregates size is DLS (*Ref International Standard ISO22412 Particle Size Analysis—Dynamic Light Scattering, International Organisation for Standardisation (ISO)* 2008). The mean hydrodynamic diameter of the nanoparticle or the aggregate of nanoparticles measured by DLS in solution is presented as size distribution by intensity (light scattering intensity is proportional to particle size) and measured at room temperature (about 25° C.).

Typically, the largest dimension or size is the diameter of a nanoparticle of round or spherical shape, or the longest length of a nanoparticle of ovoid or oval shape.

The largest dimension of a nanoparticle or aggregate as herein defined is typically between about 2 nm and about 250 nm or about 500 nm, preferably between about 4 nm or 10 nm and about 100 nm or about 200 nm, even more preferably between about (preferably at least) 10 nm and about 150 nm, between about (preferably at least) 30 nm and about 150 nm, between about (preferably at least) 40 nm and about 500 nm, between about (preferably at least) 45 nm and about 500 nm, preferably below 500 nm.

When the mean hydrodynamic diameter of the nanoparticle or the aggregate of nanoparticles in solution is measured, the DLS technique is typically used. Using DLS, the mean hydrodynamic diameter of the nanoparticle or the aggregate of nanoparticles in solution is typically between about 10 nm and about 500 nm, preferably between about 10 nm or about 30 nm and about 100 nm or about 500 nm, even more preferably between about 10 nm or about 30 nm and about 100 nm, about 150 nm, about 200 nm, about 250 nm, about 300 nm, about 350 nm, about 400 nm, about 450 nm, or about 500 nm.

When the core of the nanoparticle or nanoparticles' aggregate is measured, the electron microscopy technique is typically used. Using electron microscopy, the median largest size (also herein identified as "median largest dimension") of the core of the nanoparticle or of the nanoparticles' aggregate of the population is typically between about 5 nm and about 250 nm or about 500 nm, preferably between about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm or about 45 nm and about 75 nm, about 76 nm, about 77 nm, about 78 nm, about 79 nm, about 80 nm, about 81 nm, about 82 nm, about 83 nm, about 84 nm, about 85 nm, about 86 nm, about 87 nm, about 88 nm, about 89 nm, about 90 nm, about 91 nm, about 92 nm, about 93 nm, about 94 nm, about 95 nm, about 96 nm, about 97 nm, about 98 nm, about 99 nm, about 100 nm, about 101 nm, about 102 nm, about 103 nm, about 104 nm, about 105 nm, about 106 nm, about 107 nm, about 108 nm, about 109 nm, about 110 nm, about 111 nm, about 112 nm, about 113 nm, about 114 nm, about 115 nm, about 116 nm, about 117 nm, about 118 nm, about 119 nm, about 120 nm, about 121 nm, about 122 nm, about 123 nm, about 124 nm, about 125 nm, about 130 nm, about 140 nm, about 150 nm, about 200 nm, about 250 nm, about 300 nm, about 350 nm, about 400 nm, about 450 nm or about 500 nm.

Typically, when measuring the size of the core of the nanoparticle or nanoparticles' aggregate with electron microscopy tools, the size of the core of the nanoparticle or nanoparticles' aggregate representing the 30%-70% percentile of the population of nanoparticles and nanoparticles' aggregates is comprised between about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm or about 45 nm and about 75 nm, about 76 nm, about 77 nm, about 78 nm, about 79 nm, about 80 nm, about 81 nm, about 82 nm, about 83 nm, about 84 nm, about 85 nm, about 86 nm, about 87 nm, about 88 nm, about 89 nm, about 90 nm, about 91 nm, about 92 nm, about 93 nm, about 94 nm, about 95 nm, about 96 nm, about 97 nm, about 98 nm, about 99 nm, about 100 nm, about 101 nm, about 102 nm, about 103 nm, about 104 nm, about 105 nm, about 106 nm, about 107 nm, about 108 nm, about 109 nm, about 110 nm, about 111 nm, about 112 nm, about 113 nm, about 114 nm, about 115 nm, about 116 nm, about 117 nm, about 118 nm, about 119 nm, about 120 nm, about 121 nm, about 122 nm, about 123 nm, about 124 nm, about 125 nm, about 130 nm, about 140 nm, about 150 nm, about 200 nm, about 250 nm, about 300 nm, about 350 nm, about 400 nm, about 450 nm, about 500 nm or about 520 nm.

Composition of Nanoparticles

Nanoparticle Prepared From a Conductor Material

The nanoparticle prepared from a conductor material is an organic nanoparticle or an inorganic nanoparticle.

Inorganic nanoparticle prepared from a conductor material is typically prepared with a metallic element having a standard reduction potential E° value equal to or above about 0.01, typically when measured at 25° C. and at a pressure of 1 atm in respect to the standard hydrogen electrode (see Table 2 "reduction reactions having E° values more positive than that of the standard hydrogen electrode", 8-25, Handbook of chemistry and physics; David R. Lide; 88$^{th}$ Edition), more preferably equal to or above about 0.1, 0.2, 0.3, 0.4, or 0.5. Typical metallic elements used to prepare the nanoparticles may be selected from Tl, Po, Ag, Pd, Ir, Pt, Au, and a mixture thereof. Preferably, the metallic element usable as conductor material to prepare the nanoparticles is selected from Ir, Pd, Pt, Au, and a mixture thereof, even more preferably is selected from Au, Pt, Pd and any mixture thereof. Particularly preferred materials are Au and Pt.

Typically, gold nanoparticles have shown catalytic activity when their size was decreased to few nm (cf. M. Auffan et al., *Nature Nanotechnology* 2009, 4(10), 634-641: *Towards a definition of inorganic nanoparticles from an environmental, health and safety perspective*). In order to reduce the surface/volume ratio and thus minimize the contribution of the inorganic nanoparticle's surface to the catalytic activity, a median largest size of the core of the nanoparticle or of the nanoparticles' aggregate of the population of at least 30 nm, typically of at least 40 nm or at least 45 nm is preferred.

Organic nanoparticle prepared from a conductor material is typically prepared with an organic material having contiguous sp2 hybridized carbon centers in its structure (i.e. carbon double bond or aromatic cycles comprising heteroatoms, typically N or S, within the aromatic cycle or outside the aromatic cycle). Preferred organic materials are selected from polyaniline, polypyrrole, polyacetylene, polythiophene, polycarbazole, polypyrene, poly(3,4-ethylenedioxythiophene) and/or poly(3,4-ethylenedioxythiophene) polystyrene sulfonate.

In a particular aspect, the median largest size of the core of the nanoparticle or nanoparticles' aggregate of the population is of at least 30 nm or of at least 40 nm and preferably below 500 nm as described herein above, for example of 45 nm, when the material is a conductor material as described herein above, in particular a metallic material, typically a metal having a standard reduction potential E° above 0.2, or an organic material, typically an organic material having contiguous sp2 hybridized carbon centers in its structure, preferably a metallic material as described herein above, in particular any one of Au, Pt, Pd and any mixture thereof.

Nanoparticle Prepared From a Semiconductor Material

The nanoparticle prepared from a semiconductor material is typically an inorganic nanoparticle.

Inorganic nanoparticles are typically prepared with a semiconductor material presenting a relatively small energy band gap (Eg) between its valence and conduction bands. Typically, the semiconductor material has a band gap Eg below 3.0 eV, typically when measured at room temperature (about 25° C.) (see for instance table 12-77, Table 3; *Handbook of chemistry and physics*; David R. Lide; 88$^{th}$ Edition). In a particular aspect, the material is an intrinsic semiconductor material or an extrinsic semiconductor material as further herein described below.

Intrinsic semiconductor materials typically consist of an element from group IV A of the Mendeleev's periodic table, such as Silicon (Si) or Germanium (Ge), in a mixed composition of elements from groups III and V of the Mendeleev's periodic table, such as AlSb, AlN, GaP, GaN, InP, InN, etc., or in a mixed composition of elements from groups II and VI of the Mendeleev's periodic table, such as ZnSe, ZnTe, CdTe, etc.

Extrinsic semiconductor materials typically comprise, or consist of, an intrinsic semiconductor prepared with a high degree of chemical purity, wherein the intrinsic semiconductor material comprises a dopant.

In a particular aspect, when the nanoparticle's or nanoparticles' aggregate's extrinsic semiconductor material consists of an element from group IVA of the Mendeleev's periodic table, it is doped with a charge carrier selected from Al, B, Ga, In and P. Such extrinsic semiconductor materials may be either of n-type in which negative charge carriers dominate or of p-type in which positive charge carriers dominate. Typical extrinsic p-type semiconductor material consists of silicon (Si) or germanium (Ge) doped with a charged carrier selected from aluminum (Al), Boron (B), Gallium (Ga) and indium (In); Typical extrinsic p-type semiconductor material consists of silicon (Si) or germanium (Ge) typically doped with phosphorus (P).

Typically, the band gap energy of semiconductor nanoparticles was shown to increase when the size of the nanoparticles decreased below 10 nm (cf. M. Auffan et al., *Nature Nanotechnology* 2009, 4(10), 634-641: *Towards a definition of inorganic nanoparticles from an environmental, health and safety perspective*). In order to ensure a low surface/volume ratio and maintain a bulk band gap of the nanoparticles or nanoparticles' aggregates below 3.0 eV, a median largest size of the core of the nanoparticle or the nanoparticles' aggregate of the population of at least 30 nm, preferably of at least 40 nm, is preferred.

Thus, in a particular aspect, the median largest size of the core of the nanoparticle or nanoparticles' aggregate of the population is of at least 30 nm or of at least 40 nm and preferably below 500 nm, when the material is a semiconductor material as described herein above, in particular a semiconductor material with a band gap Eg below 3.0 eV, typically a material consisting of an element from group IVA of the Mendeleev's periodic table, in particular an element from group IVA of the Mendeleev's periodic table doped with a charge carrier selected from Al, B, Ga, In and P, or of a mixed composition of elements from group III and V of the Mendeleev's periodic table, or of a mixed composition of elements from group II and VI of the Mendeleev's periodic table.

Nanoparticle Prepared From an Insulator Material Having a High Relative Dielectric Constant (Relative Permittivity), i.e. Equal to or Above 200

The nanoparticles prepared from, or consisting of, an insulator material having a high relative dielectric constant $\varepsilon_{ijk}$ (also named relative permittivity), are typically prepared with a material having a band gap Eg equal to or above 3.0 eV typically when measured at room temperature (about 25° C.) and a relative dielectric constant $\varepsilon_{ijk}$, equal to or above 200, which is typically measured between 20° C. and 30° C. and between $10^2$ Hz up to the infrared frequency (see for instance table 12-45 "*Permittivity (dielectric constant) of inorganic solid*"; *Handbook of chemistry and physics*; David R. Lide; 88$^{th}$ Edition; Compilation of the static dielectric constant of inorganic solid. K. F. Young and H. P. R. Frederikse. *J. Phys. Chem. Ref Data, Vol.* 2, No. 2, 1973).

Such nanoparticles are typically prepared with a dielectric material which is a mixed-metal oxide preferably selected from $BaTiO_3$, $PbTiO_3$, $KTaNbO_3$, $KTaO_3$, $SrTiO_3$, $BaSrTiO_3$, etc.

Typically, the perovskite-based structure $PbTiO_3$ nanoparticles have shown a change of their paraelectric-to-ferroelectric transition temperature for nanoparticles sizes less than 20 nm-30 nm (cf. M. Auffan et al., *Nature Nanotechnology* 2009, 4(10), 634-641: *Towards a definition of inorganic nanoparticles from an environmental, health and safety perspective*). In order to ensure a low surface/volume ratio and maintain the dielectric properties of the nanoparticles or nanoparticles' aggregates, a median largest size of the core of the nanoparticle or the nanoparticles' aggregate of the population of at least 30 nm, typically of at least 40 nm, is preferred.

Thus, in a particular aspect, the median largest size of the core of the nanoparticle or nanoparticles' aggregate of the population is of at least 30 nm or of at least 40 nm and preferably below 500 nm, when the material is an insulator material as described herein above having a high relative dielectric constant $\varepsilon_{ijk}$, equal to or above 200, in particular an insulator material with a band gap Eg equal to or above 3.0 eV, preferably a mixed-metal oxide selected from $BaTiO_3$, $KTaNbO_3$, $KTaO_3$, $SrTiO_3$ and $BaSrTiO_3$.

Nanoparticle Prepared From an Insulator Material Having a Low Relative Dielectric Constant (Relative Permittivity), i.e. Equal to or Below 100

The nanoparticles prepared from, or consisting of, an insulator material having a low relative dielectric constant are typically prepared with a material having a band gap Eg equal to or above 3.0 eV typically when measured at room temperature (about 25° C.) and a relative dielectric constant $\varepsilon_{ijk}$ equal to or below 100, preferably below 50 or below 20, which is typically measured between 20° C. and 30° C. and between $10^2$ Hz up to the infrared frequency, (see for instance table 12-45 "*Permittivity (dielectric constant) of inorganic solid*"; *Handbook of chemistry and physics*; David R. Lide; 88$^{th}$ Edition; *Compilation of the static dielectric constant of inorganic solid*. K. F. Young and H. P. R. Frederikse. *J. Phys. Chem. Ref Data, Vol.* 2, No. 2, 1973).

Such nanoparticles are typically prepared with a dielectric material which is selected from a metal oxide, a mixed metal oxide, the metallic element of which is from period 3, 5 or 6 of the Mendeleev's periodic table or a lanthanide, and a carbon material. The dielectric material is preferably selected from $Al_2O_3$, $LaAlO_3$, $La_2O_3$, $SiO_2$, $SnO_2$, $Ta_2O_5$, $ReO_2$, $ZrO_2$, $HfO_2$, $Y_2O_3$ and carbon diamond. More preferably, the dielectric material is a metal oxide selected from $ReO_2$, $ZrO_2$, $HfO_2$ and any mixture thereof. Particularly preferred is a dielectric material selected from $ZrO_2$ and $HfO_2$. In a particular and preferred aspect, the dielectric material or metal oxide is not $CeO_2$ (cerium oxide), $Fe_3O_4$ (iron oxide), $SiO_2$ (silica) or any mixture thereof.

Zirconium (Zr) and hafnium (Hf) are both elements in a 4$^+$ oxidation state and, $Zr^{4+}$ and $Hf^{4+}$ elements are nearly identical in size and in chemical properties; this is the reason why, these two ions are considered together when establishing their aqueous chemistry (see chapter 8, section 8.2 *Zr4+* and *Hf4+*, p. 147 "*The hydrolysis of cations*", Bass C. F. & Mesmer R. E.; John Wiley and Sons, Inc. reprint Edition 1986).

In a particular aspect, the median largest size of the core of the nanoparticle or nanoparticles' aggregate of the population is of at least 10 nm and preferably below 500 nm as described herein above, when the material is selected from $ReO_2$, $ZrO_2$, $HfO_2$, preferably from $ZrO_2$ and $HfO_2$, and any mixture thereof, as described herein above.

The Nanoparticle'S or Nanoparticles Aggregate'S Shape

As the shape of the particle or aggregate can influence its "biocompatibility", particle or aggregate having a quite homogeneous shape is preferred. For pharmacokinetic reasons, nanoparticles or aggregates being essentially spherical, round or ovoid in shape are thus preferred. Such a shape also favors the nanoparticle's or aggregate's interaction with cells or uptake by cells. Spherical or round shape is particularly preferred.

The shape of the nanoparticle or aggregate of nanoparticles is typically evaluated using electron microscopy such as transmission electron microscopy (TEM).

The Nanoparticles' or Aggregates of Nanoparticles' Biocompatible Coating

In a preferred embodiment, the core of the nanoparticle or nanoparticles' aggregate used in the context of the present invention to prepare a composition of interest can be coated with a biocompatible material selected from an agent exhibiting stealth property. Agent exhibiting stealth properties may be an agent displaying a steric group. Such a group may be selected for example from polyacrylate; polyacrylamide (poly(N-isopropylacrylamide)); polycarbamide; a biopolymer; a polysaccharide such as dextran or xylan; and collagen. In another preferred embodiment, the core of the nanoparticles or nanoparticles' aggregates can be coated with a biocompatible material selected from an agent allowing interaction with a biological target. Such an agent can typically bring a positive or a negative charge on the nanoparticle's or nanoparticles' aggregate's surface. An agent forming a positive charge on the nanoparticle's or nanoparticles' aggregate's surface can be for example aminopropyltriethoxisilane or polylysine. An agent forming a negative charge on the nanoparticle's or nanoparticles' aggregate's surface can be for example a phosphate (for example a polyphosphate, a metaphosphate, a pyrophosphate, etc.), a carboxylate (for example citrate or dicarboxylic acid, in particular succinic acid) or a sulphate.

In a preferred embodiment, the core of the nanoparticle or aggregate of nanoparticles used in the context of the present invention presents a hydrophilic neutral surface charge or is coated with a biocompatible material (i.e. a coating agent) selected from a hydrophilic agent conferring a neutral surface charge to the nanoparticle. Indeed, when the nanoparticles of the present invention are administered to a subject, nanoparticles presenting a hydrophilic neutral surface charge or the core of the nanoparticles coated with a biocompatible agent selected from a hydrophilic agent conferring a neutral surface charge to the nanoparticles are particularly advantageous to optimize the use of the herein described nanoparticles.

A hydrophilic agent conferring neutral surface charge to the core of the nanoparticle or nanoparticles' aggregate may be an agent displaying a functional group selected from an alcohol (R—OH), an aldehyde (R—COH), a ketone (R—CO—R), an ester (R—COOR), an acid (R—COOH), a thiol (R—SH), a saccharide (glucose, fructose, ribose for instance), an anhydride (RCOOOC—R), and a pyrrole. The hydrophilic agent conferring a neutral surface charge to the core of the nanoparticle or nanoparticles' aggregate can be a monomer, a dimer, an oligomer, a polymer or a copolymer. When the agent is an oligomer, it may be an oligosaccharide such as a cyclodextrin. When the agent is a polymer, it may be a polyester (such as a poly(lactic acid) or a polyhydroxyalkanoic acid), a polyether, a polyethylene oxide, a polyethylene glycol, a polyvinylalcohol, a polycaprolactone, a polyvinylpyrrolidone, a polysaccharide such as a cellulose, a polypyrrole, etc.

In addition, a hydrophilic agent conferring neutral surface charge to the core of the nanoparticle or nanoparticles' aggregate may be an agent displaying specific groups (R—) able to interact with the surface of the nanoparticle or aggregate of nanoparticles. R is typically selected from a thiol, a silane, a carboxylic and a phosphate group.

When the core of the nanoparticle or aggregate of nanoparticles is a conductor or a semiconductor and a metallic nanoparticle, R is preferably a thiol, a thioether, a thioester, a dithiolane or a carboxylic group. Preferably, the hydrophilic neutral coating agent is selected from a thioglucose, a 2-mercaptoethanol, a 1-thioglycerol, a thiodiglycol and a hydroxybutyric acid.

When the core of the nanoparticle or aggregate of nanoparticles is an insulator, and an oxide or a mixed-oxide nanoparticle, R is preferably a silane or a phosphate group. Preferably, the hydrophilic neutral coating agent is a hydroxymethyltriethoxysilane, a fructose 6-phosphate or a glucose 6-phosphate compound.

A hydrophilic agent conferring neutral surface charge to the core of the nanoparticle or nanoparticles' aggregate may be a zwitterionic compound such as an amino acid, a peptide, a polypeptide, a vitamin or a phospholipid.

The surface charge of a nanoparticle or nanoparticles' aggregate is typically determined, as well known by the skilled person, by zeta potential measurements, typically in (a solution of) water having a concentration of nanoparticles' or nanoparticles' aggregates' material between 0.01 and 10 g/L, a pH between 6 and 8, and typically a concentration of electrolytes (in water) between 0.001 and 0.2 M, for example 0.01 M or 0.15 M. Under the herein above defined conditions, the surface charge of the nanoparticle or aggregate of nanoparticles is typically comprised between −10 mV and +10 mV (corresponding to a neutral surface charge), between −20 mV and +20 mV, or between −35 mV and +35 mV. When neutral, the surface charge of the nanoparticles or aggregate of nanoparticles is typically comprised between −10 mV, −9 mV, −8 mV, −7 mV, −6 mV, −5 mV, −4 mV, −3 mV, −2 mV, or −1 mV and 1 mV, 2 mV, 3 mV, 4 mV, 5 mV, 6 mV, 7 mV, 8 mV, 9 mV or 10 mV. When negative, the surface charge of the nanoparticles or aggregate of nanoparticles is typically below −11 mV, −12 mV, −13 mV, −14 mV −15 mV, −16 mV, −17 mV, −18 mV, −19 mV, −20 mV, −21 mV, −22 mV, −23 mV, −24 mV, −25 mV, −26 mV, −27 mV, −28 mV, −29 mV, −30 mV, −31 mV, −32 mV, −33 mV, −34 mV or −35 mV.

A full biocompatible coating of the nanoparticle or aggregate may be advantageous in the context of the present invention in order to avoid any electrical charge on the nanoparticle's surface, when the nanoparticle presents a hydrophilic neutral surface charge. The "full coating" implies the presence of a very high density/compactness of biocompatible molecules able to create at least a complete monolayer on the surface of the particle.

The biocompatible coating allows in particular the nanoparticle's stability in a fluid, such as a physiological fluid (blood, plasma, serum, etc.) or any isotonic media or physiologic medium required for a pharmaceutical administration.

Stability may be confirmed by dry extract quantification using a drying oven and measured on a nanoparticle suspension prior and after filtration, typically on a 0.45 μm filter.

Advantageously, the coating preserves the integrity of the particle in vivo, ensures or improves the biocompatibility thereof, and facilitates an optional functionalization thereof (for example with spacer molecules, biocompatible polymers, targeting agents, proteins, etc.).

The biocompatible nanoparticle or aggregate of nanoparticles of the invention should neither dissolve and release toxic species following in vivo administration (i.e. at physiological pH) nor present redox behavior, typically for said nanoparticle or aggregate of nanoparticles to be considered biocompatible, i.e. to be safely used in a subject, in particular in a mammal, preferably in a human being.

Another particular object herein described relates to a composition, in particular a pharmaceutical composition, comprising nanoparticles and/or nanoparticles' aggregates such as defined hereinabove, preferably together with a pharmaceutically acceptable carrier or vehicle.

In particular, herein described is a composition for use in enhancing brain performances or for preventing or treating/for use in prevention or treatment of pathological stress or at least one symptom thereof as herein described in a subject without exposure of the nanoparticles or nanoparticles' aggregates to an electric field, and preferably without exposure thereof to any other external activation source such as a light source, a magnetic field, or an ultrasound source, wherein the composition comprises, or consists of, nanoparticles and/or nanoparticles' aggregates and a pharmaceutically acceptable support, and wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100 as herein above described and explained.

In a preferred aspect, the composition comprises, or consists of, at least two distinct nanoparticles and/or nanoparticles' aggregates, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100.

In a typical aspect of the invention, the herein described nanoparticle(s) or aggregate(s) of nanoparticles are not used as carrier(s) of (active) therapeutic compound(s) or drug(s).

The composition can be in the form of a solid, liquid (particles in suspension), aerosol, gel, paste, and the like. Preferred compositions are in a liquid or a gel form. Particularly preferred compositions are in liquid form.

The pharmaceutically acceptable support or carrier which is employed can be any classical support for the skilled person, such as for example a saline, isotonic, sterile, buffered solution, a non-aqueous vehicle solution and the like.

The composition can also comprise stabilizers, sweeteners, surfactants, polymers and the like.

It can be formulated for example as ampoule, aerosol, bottle, tablet, capsule, by using techniques of pharmaceutical formulation known by the skilled person.

The nanoparticles or nanoparticles' aggregates of the invention can be administered to the subject using different possible routes such as intra-cranial, intra venous (IV), airways (inhalation), intra-thecal, intra-ocular or oral route (per os), intra-cerebroventricular (ICV), preferably using intra-cranial or intra-thecal.

Repeated injections or administrations of nanoparticles or nanoparticles' aggregates can be performed, when appropriate. Preferably, the nanoparticles or nanoparticles' aggregates are to be administered once.

The nanoparticles and/or nanoparticles' aggregates once administered typically interact with the neurons' subject. In a preferred aspect, this interaction is a prolonged interaction, i.e. an interaction of several hours, days, weeks or months. In a particular aspect, the nanoparticles or nanoparticles' aggregates remain in the subject.

The herein described nanoparticles, nanoparticles' aggregates, and compositions comprising such nanoparticles or nanoparticles' aggregates are for use in a subject, typically for use in an animal, preferably in a mammal, even more preferably in a human being, whatever its age or sex.

Typical quantity(ies) of nanoparticles or aggregates of nanoparticles to be administered in the cerebral cortex, hippocampus or amygdala of the subject is(are) between $10^5$ and $10^{17}$, between $10^5$ and $10^{16}$ or between $10^5$ and $10^{15}$, preferably between $10^7$ and $10^{14}$, more preferably between $10^9$ and $10^{12}$. Also, typical quantity(ies) of nanoparticles or aggregates of nanoparticles to be administered in the cerebral cortex, hippocampus or amygdala of the subject is(are) between $10^2$ and $10^{12}$ nanoparticles or aggregates of nanoparticles per $cm^3$.

Typical quantity(ies) of nanoparticles or aggregate of nanoparticles to be administered in the deep brain of the subject is(are) between $10^4$ and $10^{17}$, between $10^4$ and $10^{16}$, between $10^4$ and $10^{15}$ or between $10^4$ and $10^{14}$, preferably between $10^6$ and $10^{12}$, more preferably between $10^8$ and $10^{11}$. Also, typical quantity(ies) of nanoparticles or aggregates of nanoparticles to be administered in the deep brain of the subject is(are) between $10^1$ and $10^{11}$ nanoparticles or aggregates of nanoparticles per $cm^3$.

Also, herein described are a method for enhancing brain performances in a subject and a method for treating pathological stress or at least one symptom thereof in a subject, wherein each method comprises a step of administering anyone of the herein described nanoparticles or nanoparticles' aggregates to the subject. This method typically does not include any step of exposing the subject, and more precisely the nanoparticles or nanoparticles' aggregates which have been administered to said subject, to an electric field, and preferably also does not include any step of exposing the subject, and more precisely the nanoparticles or nanoparticles' aggregates which have been administered to said subject, to any other external activation source such as a light source, a magnetic field, or an ultrasound source.

A further object herein described relates to a kit comprising at least two distinct nanoparticles and/or nanoparticles' aggregates as herein described, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100 as herein described.

In a particular embodiment, the kit comprises, in distinct containers, distinct nanoparticles and/or nanoparticles aggregates as herein described (which are intended to be contacted, typically mixed, either in situ, i.e. on the target site, or in vitro or ex vivo before deposition of the mixture on the target site).

Also herein described is the use, in vivo, in vitro or ex vivo, of such a kit in a method as herein described for enhancing brain performances/capacities, typically for enhancing synaptic plasticity, synaptic connectivity and/or the neuronal network's memory capacity in a subject, or in a method for preventing or treating pathological stress or at least one symptom thereof in a subject in need thereof, without exposure of the nanoparticles or nanoparticles' aggregates administered to the subject to an electric field, and preferably without exposure thereof to any other external activation source such as a light source, a magnetic field, or an ultrasound source. Also, herein disclosed is a kit as herein described for use in prevention or treatment of pathological stress or of at least one symptom thereof in a subject without exposure of the nanoparticles or nanoparticles' aggregates administered to the subject to an electric field, and preferably without exposure thereof to any other external activation source such as a light source, a magnetic field, or an ultrasound source.

In a particular aspect, the nanoparticle or nanoparticles' aggregate herein described is for use in, or for use in a treatment method for, enhancing physical performances or enhancing learning, memorizing, sense perception, attention and/or decision making of a subject in need of such a treatment without exposure of said nanoparticle or nanoparticles' aggregate to an electric field, and preferably without exposure thereof to any other external activation source such as a light source, a magnetic field, or an ultrasound source.

In rodents, typically in mice, robust evidence of psychometric intelligence can be obtained from test batteries including different tasks. These tests typically include learning tasks such as odor discrimination or spatial navigation. A learning test is associated with a sensory, motor or motivational requirement imposed on the animal. For instance, to assess reasoning in mice, a test based on the concept of "fast mapping" (Carey S, et al., *Proceedings of the Standford Child Language Conference.*, 1978, 15, 17-29: *Acquiring a single new word*) can be used, to assess attentional task in mice, a "mouse Stroop test" may be used, and to assess the efficacy of working memory or working memory capacity in mice a "radial arm mazes" assay may be used (Matzel L. D et al.*Current Directions in Psychological Science,* 2013, 22(5), 342-348: *The architecture of intelligence. Converging evidence from studies of humans and animals*).

An IQ test may be used to assess memory capacity in the human being. IQ tests such as the Raven's Matrix or the Wechsler Adult Intelligence scale are well known by the skilled person and typically used to assess working memory capacity in the human being. The Stroop Color-Word Interference Test (Stroop J R, *Journal of Experimental Psychology,* 1935, 18, 643-652: *Studies of interference in serial verbal reactions*) may also be used in the human being to predict general intelligence (Huang L, et al., *Journal of Experimental Psychology: Human Perception and Performance,* 2012, 38, 414-428: *Measuring the interrelations among multiple paradigms of visual attention: an individual differences approach*).

In another particular aspect, the nanoparticle or nanoparticles' aggregate herein described is for use in enhancing neural/neurons connections, functional connectivity and/or synaptic plasticity in the brain of a subject in need of such a treatment without exposure of the nanoparticle or nanoparticles' aggregate to an electric field, and preferably without exposure thereof to any other external activation source such as a light source, a magnetic field, or an ultrasound source.

In a typical aspect, the nanoparticle or nanoparticles' aggregate herein described is for preventing or treating/for use in prevention or treatment of a subject suffering of an altered brain functional activity without exposure of the nanoparticle or nanoparticles' aggregate to an electric field, and preferably without exposure thereof to any other external activation source such as a light source, a magnetic field, or an ultrasound source.

In another particular aspect, the nanoparticle or nanoparticles' aggregate herein described is for preventing or treating/for use in prevention or treatment of a subject suffering from pathological stress or from at least one symptom thereof, in particular from chronic stress, without exposure of the nanoparticles or nanoparticles' aggregates to an electric field, and preferably without exposure thereof to any other external activation source such as a light source, a magnetic field, or an ultrasound source.

All living organisms strive towards a dynamic equilibrium, which is called homeostasis. This equilibrium is threatened by certain physical and psychological events. The interface between the incoming sensory information and the appraisal process is formed by limbic brain structures, which include the hippocampus, the amygdala, and the prefrontal cortex. Various situations may trigger stress, such as novelty, uncertainty, frustration, conflict, fear, pain, etc. Constant exposure to adverse environment involving irritants such as noise, pollution, and interpersonal conflicts may also induce stress.

Pathological stress resulting from such cumulative and/or repetitive situations alters brain cells' structure (morphology) and/or connections, and/or brain cells' functional properties. As a consequence, pathological stress severely affects health and limits the quality of human life.

Uncontrollable stress can have severe adverse repercussions and induces symptoms including deterioration in learning and memory capacity. At mild level of stress, certain neurochemical systems (for examples, catecholamines, glucocorticoids) might affect learning. As the level of stress increases (in duration and/or in intensity), several transient and permanent changes are observed in the hippocampus, including modifications in synaptic plasticity, cellular morphological changes, suppression of adult neurogenesis and/or neuronal destruction or atrophy (these changes are herein described as symptoms of pathological stress). These stress-associated changes in the brain influence learning-and-memory processes. Indeed, the hippocampus, amygdala and prefrontal cortex undergo stress-induced structural remodeling which alter behavioral and physiological responses. Chronic stress triggers atrophy of neurons in the hippocampus and prefrontal cortex, and in brain regions involved in memory, selective attention, and executive function, and causes hypertrophy of neurons in amygdala, a brain region involved in fear as well as aggressiveness. The ability to learn, remember and take decision can be compromised, and is typically decreased, by chronic stress, and may be accompanied by increased aggressiveness.

Extensive observations from in vitro and in vivo electrophysiological studies are consistent to show that stress and stress hormones impair Long Term Potentiation (LTP) (i.e. a long-lasting facilitation of neurotransmission at a synapse following natural or artificial stimulation of the synapse, which is believed to be a cellular mechanism of plasticity in the brain and to be involved especially in learning and memory).

There are many pharmaceutical agents, such as sleeping drugs, anxiolytics and beta blockers that counter act some of the problems associated with being pathologically stressed out. Likewise, drugs that reduce oxidative stress or inflammation block cholesterol synthesis or absorption and treat insulin resistance or chronic pain can help dealing with the metabolic and neurological consequences of being "pathologically stressed out". All of these medications are valuable to some degree, yet unfortunately each one has its side effects and limitations (Kim J. J. et al. *Nature Reviews Neuroscience*, 2002, 3, 453-462: *The stressed hippocampus, synaptic plasticity and lost memories*; McEwen B. X. *Physiological Review*, 2007, 87, 873-904: *Physiology and neurobiology of stress and adaptation: central role of the brain*). The herein described nanoparticles can now advantageously be used to treat a subject suffering from such pathological stress, in particular from chronic stress, typically a subject having a brain in which stress-related changes as described herein above have been detected.

The term "Treatment" refers to therapeutic treatment or measures able to prevent, alleviate or cure a pathological stress or a symptom thereof as herein above described, in particular chronic stress. Such a treatment is intended for a mammal subject, preferably a human subject in need thereof. Are considered as such, the subjects already identified (diagnosed) as suffering from a pathological stress as herein described, or those considered "at risk of developing" such pathological stress for whom the treatment is a preventive or prophylactic treatment. Particular subjects suffering from a pathological stress are the subjects who have been prescribed a drug selected from a sleeping drug, an anxiolytic and a beta blocker.

Pathological stress is distinct from oxidative stress. According to M. Auffan et al. (cf. M. Auffan et al., *Environmental Pollution* 157 (2009) 1127-1133: *Chemical Stability of metallic nanoparticles: a parameter controlling their potential cellular toxicity in vitro*), oxidative stress is a state of redox disequilibrium in which ROS (Reactive Oxygen Species) production (by the cell or by the nanoparticle itself) overwhelms the antioxidant defense capacity of the cell, thereby leading to adverse biological consequences: damage of macromolecules, lipids, DNA or proteins resulting in excess cell proliferation, apoptosis, lipid peroxidation, or mutagenesis. In cells, ROS production can be followed for example by fluorescent dyes such as dichlorofluorescein diacetate.

The examples which follow and their corresponding figures illustrate the invention without limiting the scope thereof.

FIGURES

FIG. 1. Scheme of two simplified bursts outlining some of the parameters that can be extracted from the electrical activity recording. Parameters describing general activity (spike, burst, inter burst interval (IBI) and burst period) and burst structure (burst duration, burst plateau, burst amplitude, burst inter spike interval (ISI) and burst area) are indicated. Standard deviations (SD) of these parameters are measures for regularity of general activity and burst structure respectively. Coefficient of variation in time (CVtime) reflects the temporal regularity of the activity pattern of each unit. CVtime is calculated by the ratio of parameter's standard deviation and mean. Coefficient of variation among the network (CVnet) reflects synchronization among neurons within the network. CVnet is calculated by the ratio of parameter's standard deviation by mean over the network. Large CVnet values imply a wide range of variation in the activity across the network, meaning less synchronization and higher synaptic plasticity and synaptic connectivity.

Figure 2:
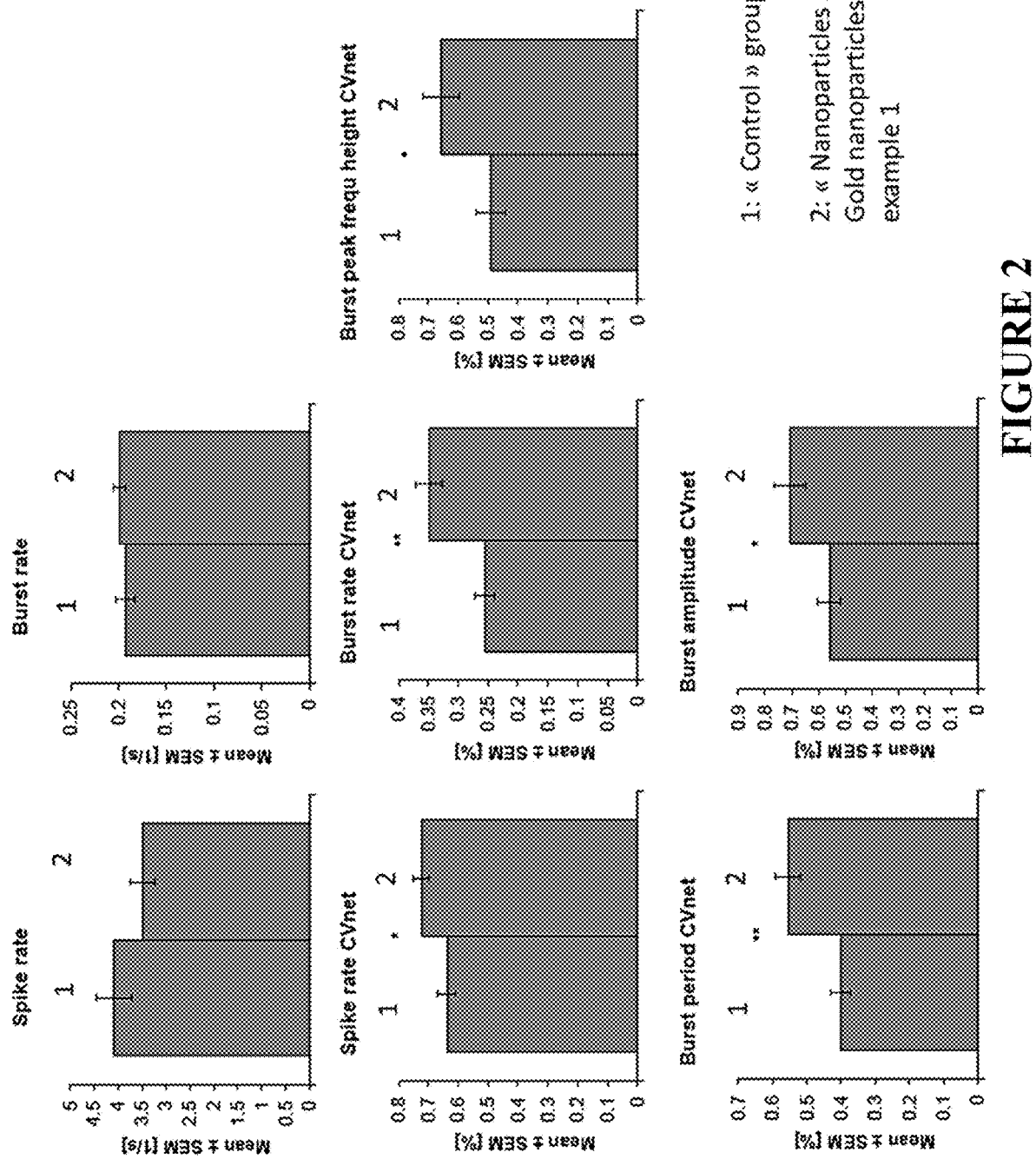

FIG. 2. Functional effects of nanoparticles from example 1 observed in the «Nanoparticles» group when compared to water used in the "Control" group on frontal cortex network activity. The results indicate higher synaptic plasticity and synaptic connectivity at the cellular level in presence of nanoparticles.

Figure 3:
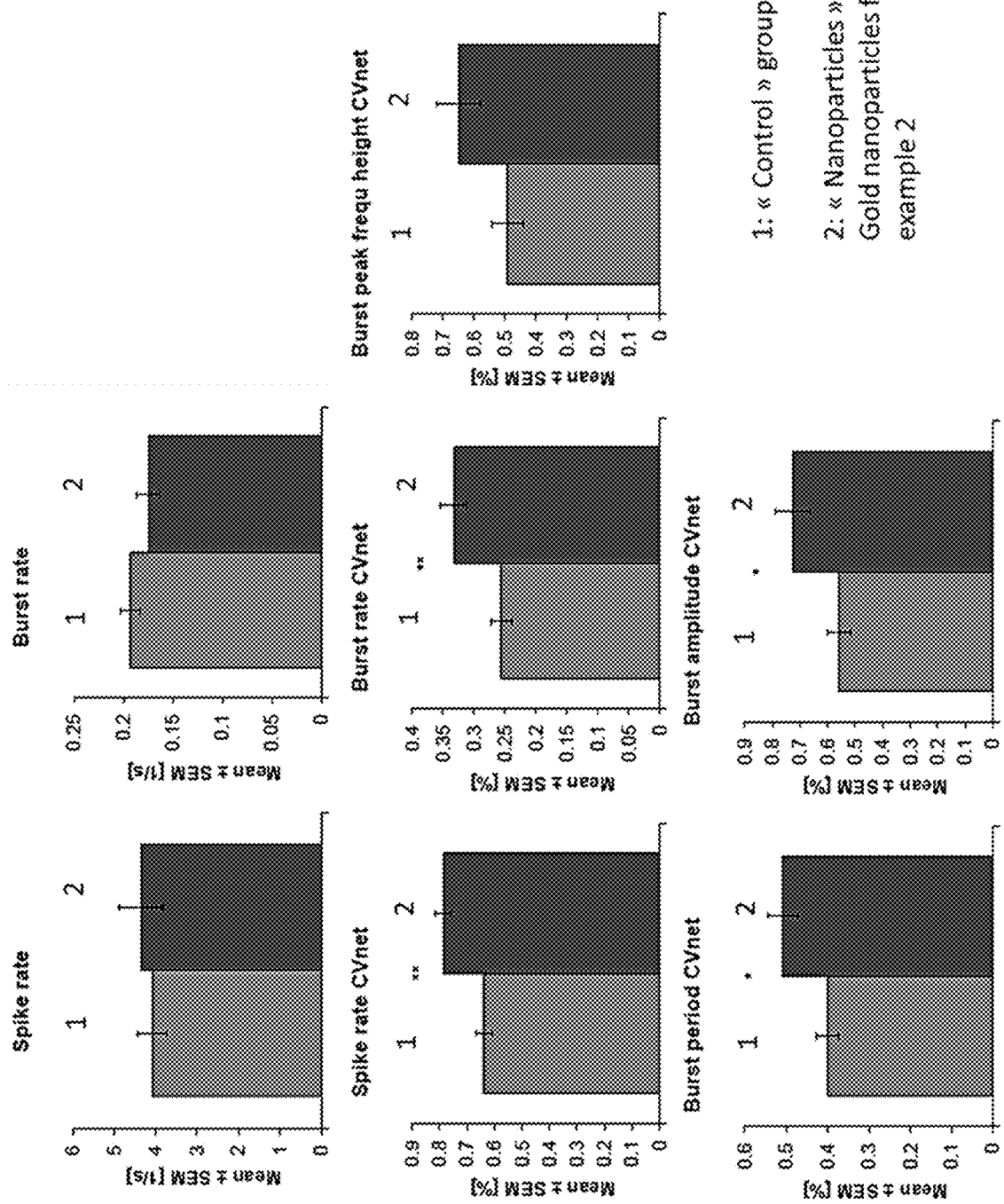

FIG. 3. Functional effects of nanoparticles from example 2 observed in the «Nanoparticles» group when compared to water used in the "Control" group on frontal cortex network activity. The results indicate higher synaptic plasticity and synaptic connectivity at the cellular level in presence of nanoparticles.

Figure 4:
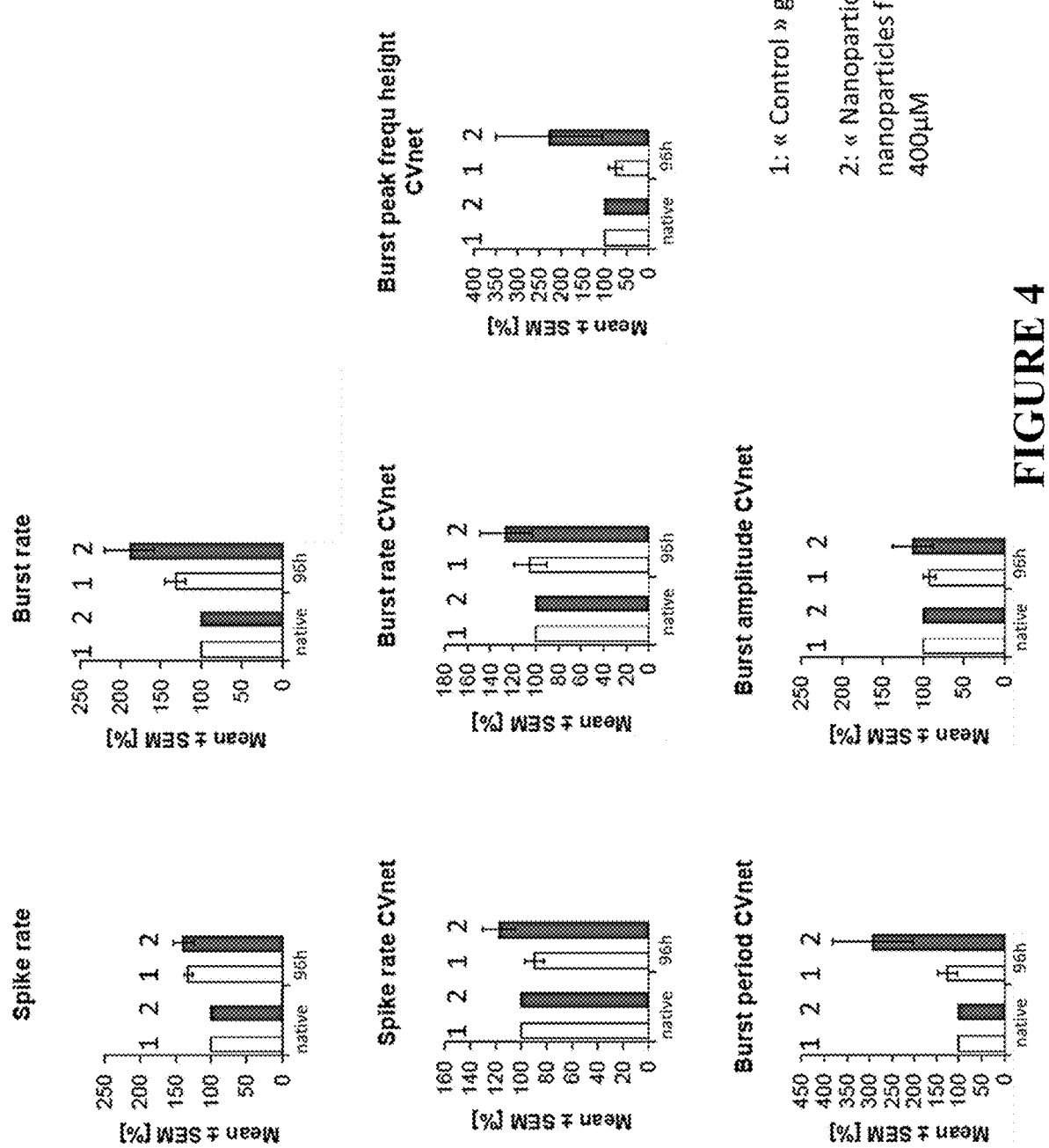

FIG. 4. Functional effects of nanoparticles from example 3 observed in the «Nanoparticles» group when compared to water used in the "Control" group on frontal cortex network activity. The results indicate higher synaptic plasticity and synaptic connectivity at the cellular level in presence of nanoparticles.

Figure 5:
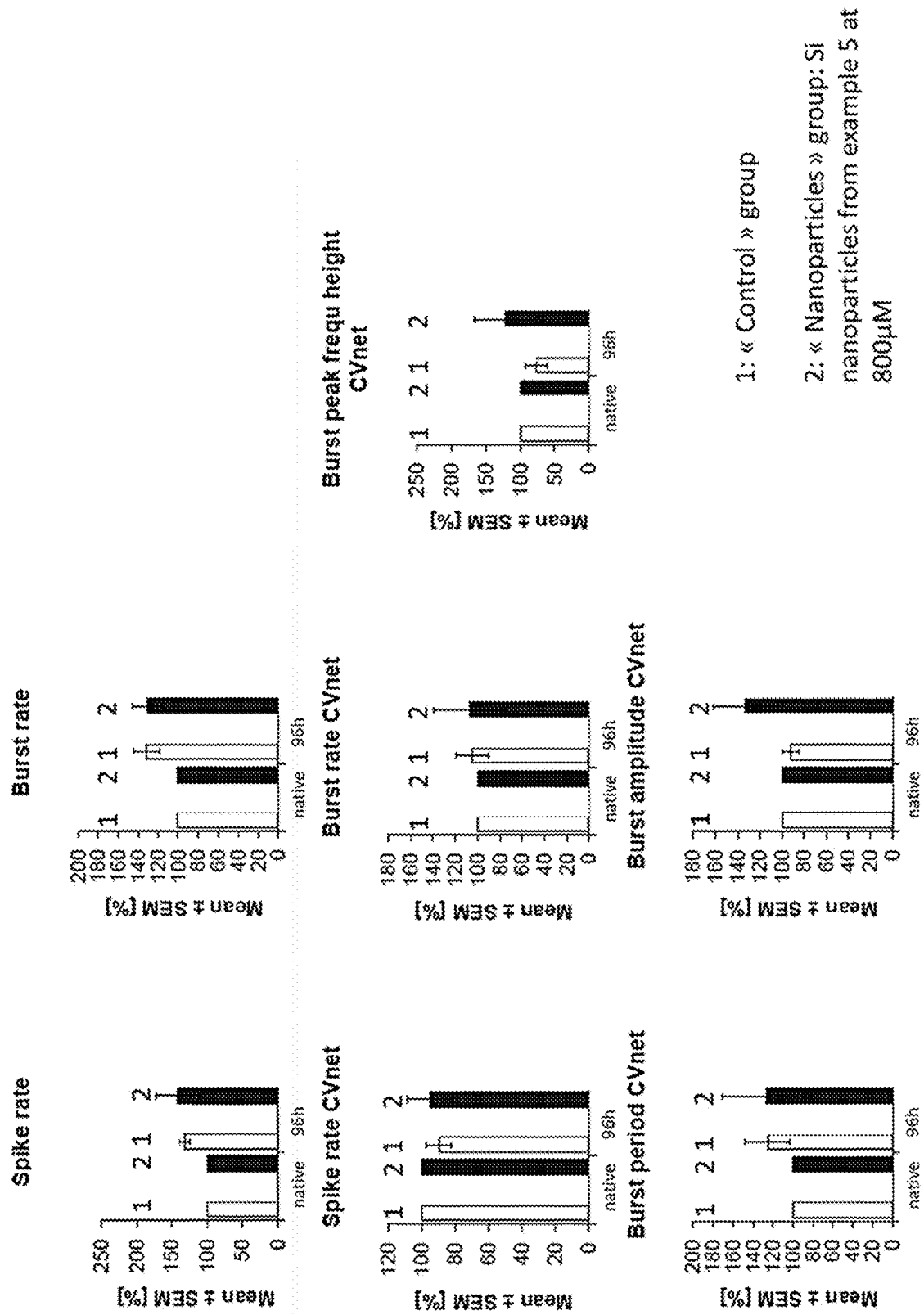

FIG. 5. Functional effects of nanoparticles from example 5 observed in the «Nanoparticles» group when compared to water used in the "Control" group on frontal cortex network activity. The results indicate higher synaptic plasticity and synaptic connectivity at the cellular level in presence of nanoparticles.

EXAMPLES

In Vitro Studies of Neurons

At the neuron level, Patch clamp technique is very useful for detecting action potentials, as it allows simultaneous direct measurement and control of membrane potential of a neuron.

This technique is used to assess the effects of nanoparticles on a single neuron.

In Vitro Studies of a Network of Neurons

Dissociated neuronal cultures coupled to multi electrode arrays (MEAs) are widely used to better understand the complexity of brain networks. In addition, the use of dissociated neuronal assemblies allows the manipulation and control of the network's connectivity (Poli D. et al, *Frontiers in Neural Circuits*, 2015, 9 (article 57), 1-14: *Functional connectivity in in vitro neuronal assemblies*).

The MEA system enables non-invasive, long-lasting, simultaneous extracellular recordings from multiple sites in the neuronal network in real time, increasing spatial resolution and thereby providing a robust measure of network activity. The simultaneous gathering of action potential and field potential data over long periods of time allows the monitoring of network functions that arise from the interaction of all cellular mechanisms responsible for spatiotemporal pattern generation (Johnstone A. F. M. et al., *Neurotoxicology* (2010), 31: 331-350, *Microelectrode arrays: a physiologically based neurotoxicity testing platform for the 21$^{st}$ century*). Compared to patch-clamp and other single electrode recording techniques, MEA measures responses of a whole network, integrating global information on the interaction of all receptors, synapses and neuronal types which are present in the network (Novellino A. et al., *Frontiers in Neuroengineering*. (2011), 4(4), 1-14, *Development of micro-electrode array based tests for neurotoxicity: assessment of interlaboratory reproducibility with neuroactive chemicals.*). As such, MEA recordings have been employed to understand neuronal communication, information encoding, propagation, and processing in neuronal cultures (Taketani, M., et al., (2006). *Advances in Network Electrophysiology*. New York, N.Y.: Springer; Obien et al., *Frontiers in Neurosciences*, 2015, 8(423): *Revealing neuronal functions through microelectrode array recordings*). The MEA technology is a sophisticated phenotypic high-content screening method to characterize functional changes in network activity in electrically active cell cultures which is very sensitive to neurogenesis, as well as to neurogenerative and neurodegenerative aspects. Moreover, neuronal networks grown on MEAs are known as being capable of responding to neuroactive or neurotoxic compounds in approximately the same concentration ranges that alter functions of an intact mammalian nervous system (Xia et al., *Alcohol*, 2003, 30, 167-174: *Histiotypic electrophysiological responses of cultured neuronal networks to ethanol*; Gramowski et al., *European Journal of Neuroscience*, 2006, 24, 455-465: *Functional screening of traditional antidepressants with primary cortical neuronal networks grown on multielectrode neurochips*; Gramowski et al., *Frontiers in Neurology*, 2015, 6(158): *Enhancement of cortical network activity in vitro and promotion of GABAergic neurogenesis by stimulation with an electromagnetic field with* 150 *MHz carrier wave pulsed with an alternating* 10 *and* 16 *Hz modulation*). This technique is used to assess the effect of nanoparticles on neuronal network(s).

In Vivo Studies of a Network of Neurons

An appropriate animal model is considered to assess the effect on the neuronal networks of animals of nanoparticles of the invention.

For instance, mazes are used to study spatial learning and memory in rats or mice. Studies using a maze helps uncover general principles about learning that can be applied to many species, including humans.

Today, mazes are typically used to determine whether different treatments or conditions affect learning and memory in rats.

Example 1

Nanoparticles Prepared With a Conductor Material: Synthesis of Gold Nanoparticles Coated With a Biocompatible Coating Having a Neutral Surface Charge Gold nanoparticles were synthesized by reducing a gold chloride salt ($HAuCl_4$) with a capping agent (sodium citrate) (protocol was adapted from G. Frens Nature Physical Science 241 (1973) 21). In a typical experiment, $HAuCl_4$ solution was heated to boiling. Subsequently, sodium citrate solution was added. The resulting solution was maintained under boiling for an additional period of 5 minutes.

A 0.22 µm filtration (filter membrane: poly(ether sulfone) (PES)) of the nanoparticles' suspension was performed and gold concentration in suspension was determined by a UV-visible spectroscopy assay at 530 nm.

A surface coating was performed using α-methoxy-ω-mercaptopoly(ethylene glycol) 20 kDa ("thiol-PEG20 kDa"). A sufficient amount of "thiol-PEG 20 kDa" was added to the nanoparticles' suspension to reach at least half a monolayer coverage (2.5 molecules/nm$^2$) on the gold nanoparticle surface. pH was adjusted between 7 and 7.2, and the nanoparticles' suspension was stirred overnight.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration: [Au]=0.1 g/L). The hydrodynamic diameter of the so obtained biocompatible gold nanoparticles in suspension was found equal to 118 nm, with a polydispersity index (dispersion of the nanoparticles' population in size) of 0.13.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [Au]=0.1 g/L). The zeta potential at pH 7 was found equal to −1 mV.

Example 2

Nanoparticles Prepared With a Conductor Material: Synthesis of Gold Nanoparticles Coated With a Biocompatible Coating Having a Negative Surface Charge Gold nanoparticles were prepared as described in example 1 (same gold inorganic core).

A 0.22 µm filtration on PES membrane filter was performed and gold concentration in suspension was determined by a UV-visible spectroscopy assay at 530 nm.

A biocompatible surface coating was performed using meso-2,3-dimercaptosuccinic acid (DMSA). A sufficient amount of DMSA was added to the nanoparticles' suspension to reach at least half a monolayer coverage (2.5 molecules/nm$^2$) on the surface. pH was adjusted between 7 and 7.2, and the nanoparticles' suspension was stirred overnight.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration: [Au]=0.1 g/L). The hydrodynamic diameter of the so obtained nanoparticles in suspension was equal to 76 nm, with a polydispersity index (dispersion of the nanoparticles' population in size) of 0.46.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [Au]=0.1 g/L). The zeta potential at pH 7 was found equal to −23 mV.

Example 3

Nanoparticles Prepared With an Insulator Material Having a Low Relative Dielectric Constant Equal to or Below 100: Synthesis Of Zirconium Oxide Nanoparticles Coated With a Biocompatible Coating Having a Neutral Surface Charge Zirconium oxide ($ZrO_2$) nanoparticles were synthesized by precipitation of zirconium chloride ($ZrCl_4$) with tetramethyl ammonium hydroxide (TMAOH) at a basic pH. The resulting suspension was transferred in an autoclave and heated at a temperature above 110° C. After cooling, the suspension was washed with deionized water and acidified.

The median largest size of the core of the nanoparticles or nanoparticles' aggregates of the population and the size of the core of the nanoparticles or nanoparticles' aggregates representing the 30%-70% percentile of the population of nanoparticles and nanoparticles' aggregates were evaluated using transmission electron microscopy and found equal to 10 nm and 8 nm-12 nm respectively. 446 nanoparticles were counted and their largest dimension was measured.

A 0.22 µm filtration on PES membrane filter was performed and ($ZrO_2$) nanoparticles' concentration was determined by drying the aqueous solution into a powder and weighing the as-obtained mass.

A biocompatible coating was prepared using silane-poly(ethylene) glycol 2 kDa ("Si-PEG 2 kDa"). A sufficient amount of "Si-PEG 2 kDa" was added to the nanoparticles' suspension to reach at least half a monolayer coverage (2.5 molecules/nm$^2$) on the surface. The nanoparticles' suspension was stirred overnight and subsequently the pH was adjusted to 7.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration of the $ZrO_2$ constituting the nanoparticle's core: [$ZrO_2$]=0.1 g/L). The nanoparticles' hydrodynamic diameter was found equal to 55 nm, with a polydispersity index (dispersion of the nanoparticles' population in size) of 0.1.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [$ZrO_2$]=0.1 g/L). The zeta potential at pH 7 was found equal to −1 mV.

Example 4

Nanoparticles Prepared With an Insulator Material Having a Low Relative Dielectric Constant Equal to or Below 100: Synthesis of Zirconium Oxide Nanoparticles Coated With a Biocompatible Coating Having a Negative Surface Charge Zirconium oxide nanoparticles were prepared as described in example 3 (same inorganic core).

A 0.22 µm filtration on PES membrane filter was performed and the ($ZrO_2$) nanoparticles' concentration was determined by drying the aqueous suspension to a powder and weighing the as-obtained mass.

Surface fractionalization was performed using sodium hexametaphosphate. A sufficient mass of sodium hexametaphosphate was added to the nanoparticles' suspension to reach at least half a monolayer coverage (2.5 molecules/nm$^2$) on the surface. The nanoparticles' suspension was stirred overnight and pH was subsequently adjusted to 7.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration of the $ZrO_2$ constituting the nanoparticle's core: [$ZrO_2$]=0.1 g/L). The nanoparticles' hydrodynamic diameter was found equal to 70 nm, with a polydispersity index (dispersion of the nanoparticles population in size) of 0.11.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: $[ZrO_2]$=0.1 g/L). The zeta potential at pH 7 was found equal to −33 mV.

Example 5

Nanoparticles Prepared With a Semiconductor Material: Silicon Nanoparticles Coated With a Biocompatible Coating Having a Neutral Surface Charge Silicon (Si) nanoparticles (powder) were obtained from US Research Nanomaterials Inc. They were coated with PVP (1% wt), representing less than 0.1 molecule/nm$^2$ on the surface.

The median largest size of the core of the nanoparticles or nanoparticles' aggregates of the population and the size of the core of the nanoparticles or nanoparticles' aggregates representing the 30%-70% percentile of the population of nanoparticles and nanoparticles' aggregates were evaluated using transmission electron microscopy and found equal to 53 nm and 45-61 nm respectively. Seventy-one (71) nanoparticles were counted and their largest dimension was measured.

Subsequently, they were coated with silane-poly(ethylene glycol) 20 kDa (Si-PEG 20 kDa) by adding a sufficient mass to obtain at least half a monolayer (2.5 molecules/nm$^2$) and by incubating the coated solution overnight at basic pH. They were subsequently dispersed in water at 30 g/L under sonication (with a probe).

A 0.22 µm filtration on PES membrane filter was performed and the (Si) nanoparticles' concentration was determined by drying the suspension to a powder and weighing the as-obtained mass.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration of the Si constituting the nanoparticle's core: $[Si]$=0.1 g/L). The nanoparticles' hydrodynamic diameter was found equal to 195 nm, with a polydispersity index (dispersion of the nanoparticles' population in size) of 0.10.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: $[Si]$=0.1 g/L). The zeta potential at pH 7 was found equal to −3 mV.

Example 6

Nanoparticles Prepared With a Semiconductor Material: Silicon Nanoparticles Coated With a Biocompatible Coating Having a Negative Surface Charge Silicon (Si) nanoparticles (powder) were obtained from US Research Nanomaterials Inc. They were coated with PVP (1% wt), representing less than 0.1 molecule/nm$^2$ on the surface.

They were dispersed in water at 30 g/L under sonication (with a probe).

A 0.22 µm filtration on PES membrane filter was performed and the (Si) nanoparticles' concentration was determined by drying the suspension to a powder and weighing the as-obtained mass.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration of the Si constituting the nanoparticle's core: $[Si]$=0.1 g/L). The nanoparticles' hydrodynamic diameter was found equal to 164 nm, with a polydispersity index (dispersion of the nanoparticles' population in size) of 0.16.

The median largest size of the core of the nanoparticles or nanoparticles' aggregates of the population and the size of the core of the nanoparticles or nanoparticles' aggregates representing the 30%-70% percentile of the population of nanoparticles and nanoparticles' aggregates were evaluated using transmission electron microscopy and found equal to 53 nm and 45-61 nm respectively. Seventy-one (71) nanoparticles were counted and their largest dimension was measured.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: $[Si]$=0.1 g/L). The zeta potential at pH 7 was found equal to −19 mV.

Example 7

Nanoparticles Prepared With an Insulator Material Having a High Relative Dielectric Constant Equal to or Above 200: Barium Titanate Nanoparticles Coated With a Biocompatible Coating Having a Negative Surface Charge Barium titanate ($BaTiO_3$) nanoparticles' suspension (20% wt in water) was obtained from US Research Materials Inc. (US3835).

Surface functionalization was performed using Silane-poly(ethylene) glycol 10 kDa ("Si-PEG 10 kDa").

Briefly, "Si-PEG 10 kDa" was first dissolved in an ethanol/water solution (⅓ v/v) and added to the $BaTiO_3$ suspension (20% wt in water) to achieve a full monolayer coverage on the surface of the nanoparticles. The suspension was sonicated and subsequently stirred overnight. After a 0.22 µm filtration (filter membrane: poly(ether sulfone)), a washing step was performed in order to eliminate unreacted "Si-PEG 10 kDa" polymers.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration of the $BaTiO_3$ constituting the nanoparticle's core: $[BaTiO_3]$=0.1 g/L). The nanoparticles' hydrodynamic diameter was found equal to 164 nm, with a polydispersity index (dispersion of the nanoparticles' population in size) of 0.16.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [BaTiO$_3$]=0.1 g/L). The zeta potential at pH 7 was found at −11 mV.

The median largest size of the core of the nanoparticles or nanoparticles' aggregates of the population and the size of the core of the nanoparticles or nanoparticles' aggregates representing the 30%-70% percentile of the population of nanoparticles and nanoparticles' aggregates were evaluated using transmission electron microscopy and found equal to 67 nm and 60-77 nm respectively. Fifty-one (51) nanoparticles were counted and their largest dimension was measured.

Example 8

Functional Evaluation of the Nanoparticles of the Invention (Nanoparticles From Examples 1 and 2) on Frontal Cortex Neuron Cultures Using Multielectrode Arrays (MEAs)

Material nd Methods

Microelectrode Array Neurochips

The 48 wells microelectrode array neurochips were purchased from Axion Biosystems Inc. These chips have 16 passive electrodes per well. The surface was coated for 1 hour with Polyethyleneimine (PEI, 50% in Borate buffer), washed and air-dried.

Primary Cell Culture, Treatment Conditions

Frontal cortex tissue was harvested from embryonic day 15/16 chr:NMRI mice (Charles River). Mice were sacrificed by cervical dislocation. Tissue was dissociated by enzymatic digestion (133.3 Kunitz units/ml DNase; 10 Units/ml Papain) and mechanical trituration, counted, vitality controlled, and plated in a 20 µl drop of DMEM containing laminin (10 µg/ml), 10% fetal bovine serum and 10% horse serum on MEAs. Cultures on MEAs were incubated at 37° C. in a 10% CO$_2$ atmosphere until ready for use. Culture media were replenished two times a week with DMEM containing 10% horse serum. The developing co-cultures were treated with the mitosis inhibitors 5-fluoro-2'-deoxyuridine (25 µM) and uridine (63 µM) on day 5 after seeding to prevent further glial proliferation.

The frontal cortex was cultured for 26 days (culture period, also identified as "native phase"). The number of active wells was quantified and the nanoparticles' suspensions ([Au]=800 µM) ("Nanoparticles" groups) or water ("Control" group) were added to the active wells. After 2 days (48 hours) of incubation, the activity was recorded for 2 hours (values were derived from 60 seconds bin data taken from a 30 minutes span).

Multichannel Recording and Multiparametric Data Analysis

For the recording, the multichannel MAESTRO recording system by Axion Biosystems (USA) was used. For extracellular recording, 48-wells MEAs were placed into the MAESTRO recording station and maintained at 37° C. Recordings were made in DMEM/10% heat inactivated horse serum. The pH was maintained at 7.4 with a continuous stream of filtered, humidified airflow with 10% CO$_2$.

Each unit represents the activity originating from one neuron recorded at one electrode. Units are separated at the beginning of the recording. For each unit, action potentials (i.e. spikes), were recorded as spike trains, which are clustered in so-called "bursts". Bursts were quantitatively described via direct spike train analysis using the programs Spike Wrangler and NPWaveX (both NeuroProof GmbH, Rostock, Germany). Bursts were defined by the beginning and end of short spike events (cf. FIG. 1).

With a multiparametric high-content analysis of the network activity patterns, 204 activity-describing spike train parameters were extracted. These parameters allow obtaining a precise description of activity changes in the following four categories: general activity, burst structure, oscillatory behavior and synchronicity.

Changes in "general activity parameters" describe the effects on action potential firing rate (spike rate), burst rate, and burst period as the time between the bursts.

"Burst structure parameters" define not only the internal structure of spikes within a high-frequency spiking phase ("burst"), e.g., spike frequency in bursts, spike rate in bursts, and burst spike density, but also the overall structure of the burst, such as duration, area, and plateau.

"Oscillatory parameters" quantify the regularity of occurrence or structure of bursts, which is calculated by coefficients of variation of primary activity parameters describing the variability of parameters (general activity, burst structure) within experimental episodes (Gramowski A. et al., Eur. J. Neurosci., 2004, 19, 2815-2825: *Substance identification by quantitative characterization of oscillator activity in murine spinal cord networks on microelectrode arrays*). Higher values indicate less regular burst structure or less regular general activity (e.g., spiking, bursting).

As a measure of synchronicity in the spike trains, "CVnet parameters" reflect "synchronization" among neurons within the network (Gramowski A. et al., Eur. J. Neurosci., 2004, 19, 2815-2825: *Substance identification by quantitative characterization of oscillator activity in murine spinal cord networks on microelectrode arrays*). CVnet is the coefficient of variation over the network. Large CVnet values imply a wide range of variation in the activity across the network, meaning less synchronization higher synaptic plasticity and synaptic connectivity. (Gramowski A. et al., Frontiers in Neurology, 2015, 6(158): *Enhancement of cortical network activity in vitro and promotion of GABAergic neurogenesis by stimulation with an electromagnetic field with 150 MHz carrier wave pulsed with an alternating 10 and 16 Hz modulation*).

CVtime reflects the periodic behavior of a single unit (a single neuron) activity pattern, whereas CVnet reveals the coordination between different neurons in a specific time frame and is a measure of synchronicity. If a population of neurons (network) is synchronized, but fluctuates in its temporal pattern, a low CVnet and a high CVtime are observed. Conversely, a non-synchronized network with several periodic patterns yields a high CVnet and a low CVtime. A high CVnet value is usually obtained under native conditions (i.e. in healthy conditions and in the absence of any treatment) when the synaptic connectivity (which designates the ensemble of chemical and electrical connections between neurons) is at a maximum.

Functional effects induced by the nanoparticles of the invention on neuronal network were evaluated through the above described parameters (also recapitulated for some of them in Table 1 below).

TABLE 1

Activity-describing parameters from the multiparametric data analysis in the two following categories: general activity and synchronicity.

| | | |
|---|---|---|
| General activity | Spike rate | Number of spikes per second, averaged over all spike trains recorded |
| | Burst rate | Number of bursts per minute, averaged over all units recorded |
| Synchronicity | Spike rate CVnet | CVnet of spike rate, reflecting network variability of spike rate within experimental episodes. A decrease of this parameter indicates an increase in synchronization within the network, whereas an increase of this parameter indicates a decreased synchronization |
| | Burst rate CVnet | CVnet of burst rate, reflecting variation of burst rate over the network during experimental episodes |
| | Burst peak frequency height CVnet | CVnet of burst duration, reflecting variation of burst duration over the network during experimental episodes |
| | Burst amplitude CVnet | CVnet of burst amplitude, reflecting the variation of burst amplitudes within burst intervals within experimental episodes over the whole network. A decrease of this parameter reflects an increase in synchronization within the network, whereas an increase of this parameter indicates a decreased synchronization |
| | Burst period CVnet | CVnet of burst period (distance between the beginning of consecutive bursts), reflecting the variation of 'burstiness' within experimental episodes over the whole network. A decrease of this parameter reflects an increase in synchronization within the network, whereas an increase of this parameter indicates a decreased synchronization |

Functional effects on network activity in the presence of the tested nanoparticles or in the absence thereof were recorded. Absolute activity values (parameter values) were expressed as mean±SEM of independent networks. For each "Nanoparticles" group or "Control" group, at least 8 active wells ("active" meaning wells with a sufficient number of electrodes measuring electrical activity) were included in the analysis. The absolute parameters' distributions were tested for normality and the statistical significance between groups was assessed via one-way ANOVA.

FIG. 2 (nanoparticles from example 1) and 3 (nanoparticles from example 2) present some representative parameters (general activity and synchronicity) characterizing functional effects observed in the "Nanoparticles" groups and in the "Control" group. Compared to water (used in the "Control" group), nanoparticles increase the variability of the network communication (increased values of CVnet parameters). This can be correlated to an enhancement of synaptic plasticity and synaptic connectivity and thus to an enhancement of the network's memory capacity.

Example 9

Functional Evaluation of the Nanoparticles of the Invention (Nanoparticles From Examples 3 and 5) on Cultures of Frontal Cortex Neurons Using Multielectrode Arrays (MEAs)

Material and Methods

Microelectrode Array Neurochips

The 48 wells microelectrode array neurochips were purchased from Axion Biosystems Inc. These chips have 16 passive electrodes per well. The surface was coated for 1 hour with Polyethyleneimine (PEI, 50% in Borate buffer), washed and air-dried.

Primary Cell Culture, Treatment Conditions

Frontal cortex tissue was harvested from embryonic day 15/16 chr:NMRI mice (Charles River). Mice were sacrificed by cervical dislocation. Tissue was dissociated by enzymatic digestion (133.3 Kunitz units/ml DNase; 10 Units/ml Papain) and mechanical trituration, counted, vitality controlled, and plated in DMEM containing 10% fetal bovine serum and 10% horse serum on poly-D-Lysine and Laminin-coated MEAs. Cultures on MEAs were incubated at 37° C. in a 10% $CO_2$ atmosphere until ready for use. Culture media were replenished two times a week with DMEM containing 10% horse serum. The developing co-cultures were treated with the mitosis inhibitors 5-fluoro-2'-deoxyuridine (25 µM) and uridine (63 µM) on day 5 after seeding to prevent further glial proliferation.

The frontal cortex was cultured for at least 4 weeks (culture period, also identified as "native phase"). The number of active wells was quantified and the nanoparticles' suspensions ([Si]=800 µM for the nanoparticles' suspension from example 5 and $[ZrO_2]$=400 µM for the nanoparticles' suspension from example 3) ("Nanoparticles" groups) or water ("Control" group) were added to the active wells. After 4 days (96 hours) of incubation, the activity was recorded for 2 hours (values were derived from 60 seconds bin data taken from a 30 minutes span).

Multichannel Recording and Multiparametric Data Analysis

For the recording, the multichannel MAESTRO recording system by Axion Biosystems (USA) was used. For extracellular recording, 48-wells MEAs were placed into the MAESTRO recording station and maintained at 37° C. Recordings were made in DMEM/10% heat inactivated horse serum. The pH was maintained at 7.4 with a continuous stream of filtered, humidified airflow with 10% $CO_2$.

Each unit represents the activity originating from one neuron recorded at one electrode. Units are separated at the beginning of the recording. For each unit, action potentials (i.e. spikes), were recorded as spike trains, which are clustered in so-called "bursts". Bursts were quantitatively described via direct spike train analysis using the programs Spike Wrangler and NPWaveX (both NeuroProof GmbH, Rostock, Germany). Bursts were defined by the beginning and end of short spike events (cf. FIG. 1).

With a multiparametric high-content analysis of the network activity patterns, 204 activity-describing spike train parameters were extracted. These parameters allow obtaining a precise description of activity changes in the following four categories: general activity, burst structure, oscillatory behavior and synchronicity.

- Changes in "general activity parameters" describe the effects on action potential firing rate (spike rate), burst rate, and burst period as the time between the bursts.
- "Burst structure parameters" define not only the internal structure of spikes within a high-frequency spiking phase ("burst"), e.g., spike frequency in bursts, spike rate in bursts, and burst spike density, but also the overall structure of the burst, such as duration, area, and plateau.
- "Oscillatory parameters" quantify the regularity of occurrence or structure of bursts, which is calculated by coefficients of variation of primary activity parameters describing the variability of parameters (general activity, burst structure) within experimental episodes (Gramowski A. et al., *Eur. J. Neurosci.*, 2004, 19, 2815-2825: *Substance identification by quantitative characterization of oscillator activity in murine spinal cord networks on microelectrode arrays*). Higher values indicate less regular burst structure or less regular general activity (e.g., spiking, bursting).
- As a measure of synchronicity in the spike trains, "CVnet parameters" reflect "synchronization" among neurons within the network (Gramowski A. et al., *Eur. J. Neurosci.*, 2004, 19, 2815-2825: *Substance identification by quantitative characterization of oscillator activity in murine spinal cord networks on microelectrode arrays*). CVnet is the coefficient of variation over the network. Large CVnet values imply a wide range of variation in the activity across the network, meaning less synchronization. (Gramowski A. et al., *Frontiers in Neurology*, 2015, 6(158): *Enhancement of cortical network activity in vitro and promotion of GABAergic neurogenesis by stimulation with an electromagnetic field with 150 MHz carrier wave pulsed with an alternating 10 and 16 Hz modulation*).

CVtime reflects the periodic behavior of a single unit (a single neuron) activity pattern, whereas CVnet reveals the coordination between different neurons in a specific time frame and is a measure of synchronicity. If a population of neurons (network) is synchronized, but fluctuates in its temporal pattern, a low CVnet and a high CVtime are observed. Conversely, a non-synchronized network with several periodic patterns yields a high CVnet and a low CVtime. A high CVnet value is usually obtained under native conditions (i.e. in healthy conditions and in the absence of any treatment) when the synaptic connectivity (which designates the ensemble of chemical and electrical connections between neurons) is at a maximum.

Functional effects induced by the nanoparticles of the invention on neuronal network were evaluated through the above described parameters (also recapitulated for some of them in Table 2 below).

TABLE 2

Activity-describing parameters from the multiparametric data analysis in the following two categories: general activity and synchronicity.

| | | |
|---|---|---|
| General activity | Spike rate | Number of spikes per second, averaged over all spike trains recorded |
| | Burst rate | Number of bursts per minute, averaged over all units recorded |
| Synchronicity | Spike rate CVnet | CVnet of spike rate, reflecting network variability of spike rate within experimental episodes. A decrease of this parameter indicates an increase in synchronization within the network, whereas an increase of this parameter indicates a decreased synchronization |
| | Burst rate CVnet | CVnet of burst rate, reflecting variation of burst rate over the network during experimental episodes |
| | Burst peak frequency height CVnet | CVnet of burst duration, reflecting variation of burst duration over the network during experimental episodes |
| | Burst amplitude CVnet | CVnet of burst amplitude, reflecting the variation of burst amplitudes within burst intervals within experimental episodes over the whole network. A decrease of this parameter reflects an increase in synchronization within the network, whereas an increase of this parameter indicates a decreased synchronization |
| | Burst period CVnet | CVnet of burst period (distance between the beginning of consecutive bursts), reflecting the variation of 'burstiness' within experimental episodes over the whole network. A decrease of this parameter reflects an increase in synchronization within the network, whereas an increase of this parameter indicates a decreased synchronization |

Functional effects on network activity in the presence of the tested nanoparticles or in the absence thereof were recorded. Activity values (parameter values) were normalized to the related native activity set at 100% for each experiment (values for the native activity were derived from 60 seconds bin data taken from a 30 minutes span after a 30 minutes stabilization activity). Relative activity values were expressed as mean±SEM of independent networks. For each "Nanoparticles" group or "Control" group, at least 8 active wells ("active" meaning wells with a sufficient number of electrodes measuring electrical activity) were included in the analysis. The absolute parameters' distributions were tested for normality and the statistical significance between groups was assessed via one-way ANOVA.

FIGS. 4 (nanoparticles from example 3) and 5 (nanoparticles from example 5) present some representative parameters (general activity and synchronicity) characterizing functional effects observed in the "Nanoparticles" groups and in the "Control" group. Compared to water (used in the "Control" group), the nanoparticles increase the variability of the network communication (increased values of CVnet parameters). This can be correlated to an enhancement of synaptic plasticity and synaptic connectivity and thus to an enhancement of the network's memory capacity.

These results highlight the advantageous performances of the nanoparticles described in the present application in enhancing functional effects (synaptic plasticity and synaptic connectivity within the neuronal network) in the neuronal network.

Example 10

Synthesis and Physico-Chemical Characterization of Gold Nanoparticles With Different Sizes Having a Neutral Surface Charge Gold nanoparticles are obtained by reduction of gold chloride with sodium citrate in aqueous solution.

Protocol was adapted from G. Frens Nature Physical Science 241 (1973) 21.

In a typical experiment, $HAuCl_4$ solution is heated to boiling. Subsequently, sodium citrate solution is added. The resulting suspension is maintained under boiling for an additional period of 5 minutes.

The nanoparticle size is adjusted from about 15 nm up to about 110 nm by carefully modifying the citrate versus gold precursor ratio (cf. Table 3).

The as prepared gold nanoparticles suspension is then concentrated using an ultrafiltration device (Amicon stirred cell model 8400 from Millipore) with cellulose membrane having an appropriate molecular weight cut-off (MWCO) and filtered through a 0.22 μm cutoff membrane filter (PES membrane from Millipore) under laminar hood.

A surface coating is performed using α-methoxy-ω-mercaptopoly(ethylene glycol) 20 kDa ("thiol-PEG20 kDa"). A sufficient amount of "thiol-PEG 20 kDa" is added to the nanoparticles' suspension to obtain a monolayer coverage on the gold nanoparticle surface. pH is adjusted between 6.8 and 7.4, and the nanoparticles' suspension is stirred overnight. Excess of thiol-PEG 20 kDa is removed using a ultrafiltration centrifugal filter (Vivaspin from Sartorius or Amicon Ultra from Merck Millipore) with an appropriate MWCO membrane under laminar hood and the final suspension is stored at 4° C.

Particle size is determined using transmission electronic microscopy by counting at least 200 nanoparticles, taking the largest nanoparticle dimension for size measurement. The median largest size of the core of the nanoparticles or nanoparticles' aggregates of the population and the size of the core of the nanoparticles or nanoparticles' aggregates representing the 30%-70% percentile of the population of nanoparticles and nanoparticles' aggregates are reported in table 3 together with the concentration of gold ([Au]) measured by Inductively-Coupled Optical Emission Spectroscopy (ICP-OES) and the zeta potential determined by measuring the electrophoretic mobility of the nanoparticles (Nano-Zetasizer, Malvern) by diluting the nanoparticles' suspension in a NaCl solution at 1 mM, at a gold concentration ([Au]) between 0.01 and 0.05 g/L and at pH about 7.

TABLE 3

| Samples | Synthesis Ratio Citrate/Au (mol/mol) | Median largest size of the core of the nanoparticle (nm) | 30%-70% percentile (nm) | Zeta potential (mV) | [Au] mg/mL (by ICP-OES) |
|---|---|---|---|---|---|
| GOLD-15 | 3.5 | 15 | 14-16 | −3 | 3.6 |
| GOLD-30 | 1.96 | 34 | 30-37 | −3 | 3.9 |
| GOLD-45 | 1.26 | 45 | 42-49 | −4 | 3.6 |
| Same nanoparticles core as nanoparticles from examples 1 & 2 | | | | | |
| GOLD-80 | 0.8 | 83 | 77-93 | −2 | 3.4 |
| GOLD-110 | 0.7 | 108 | 91-123 | −2 | 2.9 |

Example 11

Synthesis of Nanoparticles Prepared With a Conductor Material:
Poly(3,4-ethylenedioxythiophene) Nanoparticles (PEDOT Nanoparticles) Having a Negative Surface Charge Poly(3,4-ethylenedioxythiophene) nanoparticles (PEDOT nanoparticles) dispersion in water (1.1% w/w) were obtained from Sigma (sigma 675288) and used as such.

The zeta potential was determined by measuring the electrophoretic mobility of the nanoparticles (Nano-Zetasizer, Malvern) by diluting the nanoparticles' suspension in a NaCl solution at 1 mM at pH 7.3 (final PEDOT concentration: 1 g/L). The zeta potential at pH 7.3 was found equal to −53 mV.

The median largest dimension of the nanoparticles or nanoparticles' aggregates of the population and the size of the core of the nanoparticles or nanoparticles' aggregates representing the 30%-70% percentile of the population of nanoparticles and nanoparticles' aggregates were evaluated using scanning electron microscopy (SEM) and were equal to 408 nm and 311 nm-518 nm respectively (56 nanoparticles were counted and their largest dimension was measured).

Example 12

Synthesis of Nanoparticles Prepared With an Insulator Material Having a Low Relative Dielectric Constant Equal to or Below 100:
Synthesis of Hafnium Oxide Nanoparticles Coated With a Biocompatible Coating Having a Negative Surface Charge Hafnium oxide ($HfO_2$) nanoparticles were synthesized by precipitation of Hafnium chloride ($HfCl_4$) with tetramethyl ammonium hydroxide (TMAOH) at a basic pH. The resulting suspension was transferred in an autoclave and heated at a temperature above 110° C. After cooling, the suspension was washed with deionized water and acidified.

Surface functionalization was performed using sodium hexametaphosphate. A sufficient mass of sodium hexametaphosphate was added to the nanoparticles' suspension to reach at least half a monolayer coverage (2.5 molecules/$nm^2$) on the surface. The nanoparticles' suspension was stirred overnight and pH was subsequently adjusted to 7.

The invention claimed is:

1. A method for enhancing brain performance or for preventing or treating pathological stress in a subject, wherein the method comprises a step of administering a nanoparticle or nanoparticle aggregate, or a composition comprising nanoparticles and/or nanoparticle aggregates and a pharmaceutically acceptable support, to a subject, the nanoparticle or nanoparticle aggregate material being selected from a conductor material selected from a metal having a standard reduction potential E° above 0.2 and an organic material having contiguous sp2 hybridized carbon centers in its structure, a semiconductor material with a band gap Eg below 3.0 eV selected from an element from group IVA of the Mendeleev's periodic table and a mixed composition of elements from groups III and V of the Mendeleev's periodic table, a mixed-metal oxide insulator material with a dielectric constant $\varepsilon_{ijk}$ equal to or above 200, and an insulator material with a dielectric constant $\varepsilon_{ijk}$ equal to or below 100 selected from $Al_2O_3$, $LaAlO_3$, $La_2O_3$, $SiO_2$, $SnO_2$, $Ta_2O_5$, $ReO_2$, $ZrO_2$, $HfO_2$, $Y_2O_3$ and carbon diamond, the relative dielectric constant $\varepsilon_{ijk}$ beinig measured between 20° C. and 30° C. and between $10^2$ Hz up to the infrared frequency, wherein i) the median largest size of the core of the nanoparticle or nanoparticle aggregate of the population is of at least 30 nm when the material is a conductor material, a semiconductor material or an insulator material with a dielectric constant $\varepsilon_{ijk}$ equal to or above 200, wherein ii) the core of the nanoparticle or nanoparticle aggregate is coated with a biocompatible coating providing a neutral or a negative surface charge when measured in a solution of water having a concentration of electrolytes between 0.001 and 0.2 M, a concentration of the nanoparticle or nanoparticle aggregate material between 0.01 and 10 g/L and a pH between 6 and 8, wherein iii) the nanoparticle or nanoparticle aggregate is not used as carrier of therapeutic compound(s) or drug(s), and wherein iv) the method does not include any step of exposing the nanoparticle or nanoparticle aggregate to an electric field nor to any other external activation source.

2. The method according to claim 1, wherein the nanoparticle or nanoparticle aggregate material is selected from a metallic nanoparticle wherein the metallic element is Ir, Pd, Pt, Au, or any mixture thereof, and an organic nanoparticle consisting of polyaniline, polypyrrole, polyacetylene, polythiophene, polycarbazole and/or polypyrene.

3. The method according to claim 1, wherein the material consists of an element from group IVA of the Mendeleev's periodic table, and said element is silicon (Si) or Germanium (Ge).

4. The method according to claim 1, wherein the nanoparticle or nanoparticle aggregate material is an element from group IVA of the Mendeleev's periodic table and is doped with a charge carrier selected from Al, B, Ga, In and P.

5. The method according to claim 1, wherein the material is an insulator material with a band gap Eg equal to or above 3.0 eV.

6. The method according to claim 5, wherein the insulator material with a relative dielectric constant $\varepsilon_{ijk}$ equal to or above 200 is a dielectric material which is a mixed-metal oxide selected from $BaTiO_3$, $KTaNbO_3$, $KTaO_3$, $SrTiO_3$ and $BaSrTiO_3$.

7. The method according to claim 5, wherein the material is an insulator material with a relative dielectric constant $\varepsilon_{ijk}$ equal to or below 100 is a metal oxide selected from $ReO_2$, $ZrO_2$ and $HfO_2$.

8. The method according to claim 1, wherein the method is for enhancing physical performance, or enhancing learning, memorizing, sense perception, attention and/or decision making of a subject.

9. The method according to claim 1, wherein the composition comprises at least two distinct nanoparticles or nanoparticle aggregates.

10. A composition or kit comprising at least two distinct nanoparticles or nanoparticle aggregates, the nanoparticle or nanoparticle aggregate material being selected from a conductor material selected from a metal having a standard reduction potential E° above 0.2 and an organic material having contiguous sp2 hybridized carbon centers in its structure, a semiconductor material with a band gap Eg below 3.0 eV selected from an element from group IVA of the Mendeleev's periodic table and a mixed composition of elements from groups III and V of the Mendeleev's periodic table, a mixed-metal oxide insulator material with a dielectric constant $\varepsilon_{ijk}$, equal to or above 200, and an insulator material with a dielectric constant $\varepsilon_{ijk}$, equal to or below 100 selected from $Al_2O_3$, $LaAlO_3$, $La_2O_3$, $SiO_2$, $SnO_2$, $Ta_2O_5$, $ReO_2$, $ZrO_2$, $HfO_2$, $Y_2O_3$ and carbon diamond, the relative dielectric constant $\varepsilon_{ijk}$ being measured between 20° C. and 30° C. and between $10^2$ Hz up to the infrared frequency, wherein i) the median largest size of the core of the nanoparticle or nanoparticle aggregate of the population is of at least 30 nm when the material is a conductor material, a semiconductor material or an insulator material with a dielectric constant $C_{ijk}$ equal to or above 200 wherein ii) the core of the nanoparticle or nanoparticle aggregate is coated with a biocompatible coating providing a neutral or a negative surface charge when measured in a solution of water having a concentration of electrolytes between 0.001 and 0.2 M, a concentration of the nanoparticle or nanoparticle aggregate material between 0.01 and 10 g/L and a pH between 6 and 8, and wherein iii) the nanoparticles or nanoparticle aggregates are not used as carrier of therapeutic compound(s) or drug(s).

* * * * *

UNITED STATES PATENT AND TRADEMARK OFFICE
CERTIFICATE OF CORRECTION

| | |
|---|---|
| PATENT NO. | : 11,471,482 B2 |
| APPLICATION NO. | : 16/955096 |
| DATED | : October 18, 2022 |
| INVENTOR(S) | : Agnes Pottier, Laurent Levy and Marie-Edith Meyre |

It is certified that error appears in the above-identified patent and that said Letters Patent is hereby corrected as shown below:

In the Specification

<u>Column 10,</u>
Line 36, "Aggregate'S" should read --Aggregate's--.

<u>Column 16,</u>
Line 1, "Bass C.F." should read --Baes C.F.--.
Line 11, "The Nanoparticle'S or Nanoparticles Aggregate'S" should read --The Nanoparticle's or Nanoparticles Aggregate's--.

Signed and Sealed this
Fifteenth Day of August, 2023

Katherine Kelly Vidal
*Director of the United States Patent and Trademark Office*